United States Patent
Whitten et al.

(10) Patent No.: US 11,882,831 B2
(45) Date of Patent: Jan. 30, 2024

(54) SUBSTITUTED THIOPHENE OLIGOMERS AND POLYMERS

(71) Applicant: UNM Rainforest Innovations, Albuquerque, NM (US)

(72) Inventors: David G. Whitten, Albuquerque, NM (US); Dylan Brown, Albuquerque, NM (US); Jianzhong Yang, Albuquerque, NM (US); Edward Strach, Albuquerque, NM (US); Mohammed Khalil, Albuquerque, NM (US)

(73) Assignee: UNM Rainforest Innovations, Redmond, WA (US)

( * ) Notice: Subject to any disclaimer, the term of this patent is extended or adjusted under 35 U.S.C. 154(b) by 0 days.

(21) Appl. No.: 17/448,635

(22) Filed: Sep. 23, 2021

(65) Prior Publication Data

US 2022/0132843 A1    May 5, 2022

Related U.S. Application Data

(62) Division of application No. 16/648,910, filed as application No. PCT/US2018/052014 on Sep. 20, 2018, now Pat. No. 11,154,059.

(60) Provisional application No. 62/724,429, filed on Aug. 29, 2018, provisional application No. 62/562,272, filed on Sep. 22, 2017.

(51) Int. Cl.
| | | |
|---|---|---|
| *A01N 43/10* | (2006.01) | |
| *A01N 25/34* | (2006.01) | |
| *A01N 43/50* | (2006.01) | |
| *A61L 2/08* | (2006.01) | |
| *C08G 61/12* | (2006.01) | |

(52) U.S. Cl.
CPC ............ *A01N 43/10* (2013.01); *A01N 25/34* (2013.01); *A01N 43/50* (2013.01); *A61L 2/08* (2013.01); *C08G 61/126* (2013.01); *A61L 2300/404* (2013.01); *C08G 2261/143* (2013.01); *C08G 2261/149* (2013.01); *C08G 2261/224* (2013.01); *C08G 2261/3223* (2013.01)

(58) Field of Classification Search
None
See application file for complete search history.

(56) References Cited

U.S. PATENT DOCUMENTS

| | | |
|---|---|---|
| 6,569,952 B1 | 5/2003 | Chen et al. |
| 8,455,265 B2 | 6/2013 | Whitten et al. |
| 8,618,009 B2 | 12/2013 | Schanze et al. |
| 9,005,540 B2 | 4/2015 | Schanze et al. |
| 9,125,415 B2 | 9/2015 | Schanze et al. |
| 9,527,806 B2 | 12/2016 | Whitten et al. |
| 9,679,672 B2 | 6/2017 | Levi et al. |
| 9,750,250 B2 | 9/2017 | Whitten et al. |
| 10,058,099 B2 | 8/2018 | Whitten et al. |
| 10,092,000 B2 | 10/2018 | Whitten et al. |
| 10,174,042 B2 | 1/2019 | Whitten et al. |
| 10,638,759 B2 | 5/2020 | Whitten et al. |
| 11,154,059 B2 | 10/2021 | Whitten et al. |
| 2005/0148254 A1 | 7/2005 | Lu et al. |
| 2008/0085210 A1 | 4/2008 | Griesbach et al. |
| 2012/0271023 A1 | 10/2012 | Whitten et al. |
| 2013/0330386 A1 | 12/2013 | Whitten et al. |
| 2016/0222150 A1* | 8/2016 | Whitten .............. C07D 233/64 |
| 2016/0244554 A1 | 8/2016 | Cheng |
| 2020/0245619 A1 | 8/2020 | Whitten et al. |

FOREIGN PATENT DOCUMENTS

| | | |
|---|---|---|
| EP | 2051750 B1 | 3/2017 |
| WO | WO-2019060586 A1 | 3/2019 |

OTHER PUBLICATIONS

"", Antimicrobial resistance: global report on surveillance, World Health Organization, (2014), 256 pgs.
"U.S. Appl. No. 16/648,910, Final Office Action dated Dec. 24, 2020", 13 pgs.
"U.S. Appl. No. 16/648,910, Non Final Office Action dated Sep. 11, 2020", 12 pgs.
"U.S. Appl. No. 16/648,910, Notice of Allowance dated Jun. 25, 2021", 9 pgs.
"U.S. Appl. No. 16/648,910, Response filed May 24, 2021 to Final Office Action dated Dec. 24, 2020", 17 pgs.
"U.S. Appl. No. 16/648,910, Response filed Aug. 26, 2020 to Restriction Requirement dated Jun. 26, 2020", 9 pgs.
"U.S. Appl. No. 16/648,910, Response filed Dec. 2, 2020 to Non Final Office Action dated Sep. 11, 2020", 12 pgs.
"U.S. Appl. No. 16/648,910, Restriction Requirement dated Jun. 26, 2020", 8 pgs.
"International Application Serial No. PCT/US2018/052014, International Preliminary Report on Patentability dated Apr. 2, 2020", 6 pgs.
"International Application Serial No. PCT/US2018/052014, International Search Report dated Dec. 27, 2018", 3 pgs.
"International Application Serial No. PCT/US2018/052014, Written Opinion dated Dec. 27, 2018", 4 pgs.
Alvarez, M, et al., "Photodynamic Inactivation of Candida Albicans Using Bridged (Polysilsesquioxane Films Doped with Porphyrin", Bioorganic & Medicinal Chemistry 20, (2012), 4032-4039.
Ballatore, M, et al., "Photodynamic Inactivation of Bacteria Using Novel Electrogenerated Porphyrin-Fullerene C60 Polymeric Films", Environ. Sci. Technol. 49, (2015), 7456-746.
Bozja, J, et al., "Porphyrin-based, light-activated antimicrobial materials", J. Polym. Sci. A Polym. Chem. 41, (2003), 2297-2303.

(Continued)

*Primary Examiner* — Craig D Ricci
(74) *Attorney, Agent, or Firm* — Schwegman Lundberg & Woessner, P.A.

(57) ABSTRACT

The present disclosure provides an antimicrobial substrate including a substrate and a polythiophene polymer. The polythiophene polymer has a number of repeated monomer units from n is 5-14 or 30 to 120, a number average molecular weight (Mn) from 1,000 to 4,000 or 10,000 to 40,000; and a polydispersity index (PDI) from 1 to 1.3. The present disclosure also provides the polythiophene polymer and uses thereof.

20 Claims, 5 Drawing Sheets

(56) References Cited

OTHER PUBLICATIONS

Funes, Matias, et al., "Photodynamic Properties and Photoantimicrobial Action of Electrochemically Generated Porphyrin Polymeric Films", Environ. Sci. Technol., 43 (3), (2009), 902-908.

Guo, C, et al., "H2O2 and/or TiO2 photocatalysis under UV irradiation for the removal of antibiotic resistant bacteria and their antibiotic resistance genes", J. Hazard. Mater. 323, (2017), 710-718.

Hamblin, Michael, "Antimicrobial photodynamic inactivation: a bright new technique to kill resistant microbes", Current Opinion in Microbiology 33, (2016), 67-73.

Huang, Y, et al., "Selective Imaging and Inactivation of Bacteria over Mammalian Cells by Imidazolium-Substituted Polythiophene", Chem. Mater. 29, (2017), 6389-6395.

Huynh, T P, et al., "Functionalized polythiophenes: Recognition materials for chemosensors and biosensors of superior sensitivity, selectivity and detectability", ?Prog. Polym. Sci. 47, (2015), 1-25.

Jain, A, et al., "Antimicrobial Polymers", Adv. Healthc. Mater. 3(12), (2014), 1969-1985.

Ji, Eunkyung, et al., "Antibacterial Activity of Conjugated Polyelectrolytes with Variable Chain Lengths", Langmuir, 27, (2011), 10763-10769.

Lan, M, et al., "Water-soluble polythiophene for two-photon excitation fluorescence imaging and photodynamic therapy of cancer", ACS Appl. Mater. Interfaces 9(17), (2017), 14590- 14595.

Lin, Jui-Teng, "Progress of nanotechnology for phototherapy: Fundamentals and applications", Medical Devices and Diagnostic Engineering vol. 4(1), (2017), 101-107.

Masilelaa, N, et al., "Photodynamic Inactivation of *Staphylococcus aureus* Using Low (Symmetrically Substituted Phthalocyanines Supported on a Polystyrene Polymer Fiber", Dyes Pigm. 96, (2013), 500-508.

Muñoz-Bonilla,, A, et al., "The roadmap of antimicrobial polymeric materials in macromolecular nanotechnology", Eur. Polym. J. 65, (2015), 46-62.

Perepichka, I F, et al., "Light-Emitting Polythiophenes", Adv. Mater. 17, (2005), 2281-2305.

Sella, Sandra, et al., "Bacillus atrophaeus: Main Characteristics and Biotechnological Applications—a Review", Crit. Rev. Biotechnol. 35(4), (2014), 533-545.

Smith, Rachel, et al., "Antibiotic Resistance: a Primer and Call to Action", Health Commun. 30(3), (2015), 309-314.

Spellberg, Brad, et al., "The epidemic of antibiotic-resistant infections: a Call to Action for the Medical Community from the Infectious Diseases Society of America", Clin. Infect. Dis. 46(2), (2008), 155-164.

Taj, Muhammad K., et al., "*Escherichia coli* as a Model Organism", Int. J. Engg. Res. & Sci. & Tech. 3(2), [Online]. Retrieved from the Internet: <URL: http://www.ijerst.com/currentissue.php>, (2014), 1-8.

Tang, Y, et al., "Light-Induced Antimicrobial Activity of Symmetrical and Asymmetrical Oligophenylene Ethynylenes". Langmuir 27, (2011), 4956-4962.

Tempesti, Tomas, et al., "Poly(propylene)-based Films Modified with a Tetracationic Phthalocyanine Phthalocyanine with Applications in Photodynamic Inactivation of Candida albicans", Polym.-Plast. Techn. Engin. 57, (2018), 166-174.

Wainwright, Mark, et al., "Photoantimicrobials—are we afraid of the light?", Lancet. Infect. Dis. 17(2), [Online]. Retrieved from the Internet: <URL: www.thelancet.com/infection>, (Feb. 2017), e49-e55.

Wainwright, Mark, "Photodynamic antimicrobial chemotherapy (PACT)", J. Antimicrob. Chemother 42, (1998), 13-28.

Walker, Tim, et al., "A light-activated antimicrobial surface Is Active Against Bacterial, (Viral and Fungal Organisms", Sci. Rep, 7(1), 15298, (2017), 10 pgs.

Wang, J, et al., "Assessing the Biocidal Activity and Investigating the Mechanism of Oligo p phenylene-ethynylenes", ACS Appl. Mater. Interfaces 9, (2017), 7964-7971.

Zhou, Z, et al., "End-Only Functionalized Oligo(phenylene ethynylene)s: Synthesis Photophysical and Biocidal Activity", J. Phys. Chem. Lett., 1, (2010), 3207-3212.

U.S. Appl. No. 16/648,910, filed Mar. 19, 2020, Substituted Thiophene Oligomers and Polymers.

\* cited by examiner

SUBSTITUTED THIOPHENE OLIGOMERS AND POLYMERS

CROSS-REFERENCE TO RELATED APPLICATIONS

This application is a divisional of U.S. patent application Ser. No. 16/648,910, filed Mar. 19, 2020, which is a U.S. National Stage Filing under 35 U.S.C. 371 from International Application No. PCT/US2018/052014, filed Sep. 20, 2018, and published as WO 2019/060586 on Mar. 28, 2019, which application claims the benefit of priority to U.S. Provisional Patent Application Ser. No. 62/562,272, filed Sep. 22, 2017, and U.S. Provisional Patent Application Ser. No. 62/724,429, filed Aug. 29, 2018, each of which are incorporated by reference herein in their entirety.

STATEMENT OF GOVERNMENT SUPPORT

This invention was made with Government support under Contract No. DE-SC0016353 awarded by the U.S. Department of Energy. The U.S. Government has certain rights in this invention.

BACKGROUND

Antibiotic resistant bacteria have been acknowledged by the World Health Organization, Center for Disease Control, and Infectious Diseases Society of America as a major threat to public health, with the potential to lead to widespread, untreatable, infection. Significant effort has been dedicated to identifying bactericidal agents having modes of action which do not trigger resistance. Polymeric photosensitizers and polyelectrolytes are a class of compounds which have attracted attention due to their strong activity as antimicrobials, low toxicity to mammalian cells, and ability to play the role of photosensitizers in photodynamic therapy. Such compounds can be incorporated into materials and liquids compositions. Such compounds can result in rapid and profound damage to both the cell envelope and cytoplasmic components of bacteria and yet their mode of activity does not rely on a specific cell surface or active site interaction. In some cases, these compounds can absorb light in the visible and near infrared range to excite triplet oxygen and generate reactive oxygen species (ROS) such as peroxides, singlet oxygen, and hydroxyl radicals, which are generically cytotoxic which thus allows the compounds to be used as potent antimicrobial compounds which do not trigger resistance. For this reason, polymeric photosensitizers and polyelectrolytes are promising agents for killing antibiotic resistant strains.

There remains a need to for new antibacterial agents for use in materials and methods which broadly kill bacteria via mechanisms that do not give rise to resistance.

SUMMARY OF THE INVENTION

In various embodiments, the present disclosure provides a polythiophene polymer having the structure of Formula I:

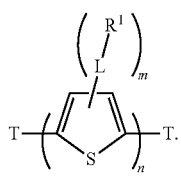

In formula I, $R^1$ can be

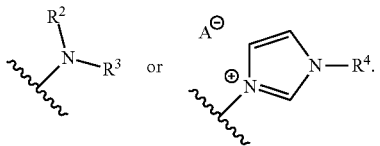

In formula I, each of $R^2$ and $R^3$ can be independently $C_1$-$C_6$ alkyl or $R^2$ and $R^3$ taken together can be linked $C_2$-$C_5$ alkyl which forms a 3 to 6-membered saturated heterocyclic ring together with the nitrogen at which they attach. In formula I $R^4$ can be $C_1$-$C_6$ alkyl, A can be a counterion. L can be a divalent $C_1$-$C_{20}$ alkyl linker, optionally interrupted by 1, 2 or 3 oxygen, sulfur or nitrogen atoms, T can be a terminal group. Furthermore in formula I, m can be 1-2 and n can be 5-14 or 30 to 120. The polymer mixture can have a number average molecular weight (Mn) from 1,000 to 4,000 or 10,000 to 40,000. The polymer mixture further can have a polydispersity index (PDI) from 1 to 1.3.

The present disclosure also provides an antimicrobial substrate, comprising a substrate and a polythiophene having the structure of formula I:

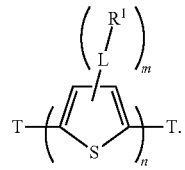

In formula I, $R^1$ can be

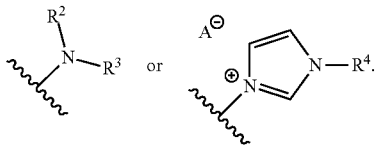

Each of $R^2$ and $R^3$ can be independently $C_1$-$C_6$ alkyl or $R^2$ and $R^3$ taken together can be linked $C_2$-$C_5$ alkyl which forms a 3 to 6-membered saturated heterocyclic ring together with the nitrogen at which they attach. In formula I, $R^4$ can be $C_1$-$C_6$ alkyl. A can be a counterion. L can be a divalent $C_1$-$C_{20}$ alkyl linker, optionally interrupted by 1, 2 or 3 oxygen, sulfur or nitrogen atoms. T can be a terminal group. Furthermore, m can be 1-2 and n can be 30 to 120. The polythiophene can have a number average molecular weight (Mn) from 10,000 to 40,000 and the polythiophene can have a polydispersity index (PDI) is from 1 to 1.3.

The present disclosure also provides a method of disinfecting, comprising treating a surface with a disinfectant composition which comprises a carrier and a polythiophene having the structure In formula I, $R^1$ can be

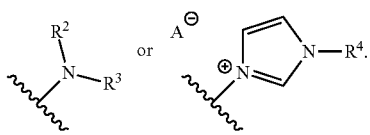

Each of $R^2$ and $R^3$ can be independently $C_1$-$C_6$ alkyl or $R^2$ and $R^3$ can be taken together are linked $C_2$-$C_5$ alkyl which forms a 3 to 6-membered saturated heterocyclic ring together with the nitrogen at which they attach. In formula I, $R^4$ can be $C_1$-$C_6$ alkyl, A can be a counterion and L can be a divalent $C_1$-$C_{20}$ alkyl linker, optionally interrupted by 1, 2 or 3 oxygen, sulfur or nitrogen atoms. T can be a terminal group. Furthermore, m can be 1-2 and n can be 5-14 or 30 to 120. The polythiophene can have a number average molecular weight (Mn) from 1,000 to 4,000 or 10,000 to 40,000 and the polythiophene can have a polydispersity index (PDI) is from 1 to 1.3.

Advantages, some of which are unexpected, are achieved by various embodiments of the present disclosure. Various embodiments of the present disclosure can provide a substrate which has antimicrobial activity under light and dark conditions effective against antibiotic resistant bacteria and which does not trigger antibiotic resistance in bacteria. For example, in various embodiments, the antimicrobial substrates can be passively or actively photoactivated to generate cytotoxic oxygen species. In various embodiments, the present disclosure provides antimicrobial substrates for which light absorbance can be advantageously tuned for the appropriate need or use. For example, in various embodiments use of large polythiophenes can provide a substrate which passively photoactivates with visible light or use of smaller polythiophenes, or complexed polythiophenes, can provide a substrate which is photoactivated upon exposure to ultraviolet (UV) light. The antimicrobial substrates of the present disclosure can be configured to retain antimicrobial polythiophenes, which is advantageous for providing reusable compositions or substrates having washable, antimicrobial surfaces. The antimicrobial substrates of the present disclosure can also be configured to deposit antimicrobial polythiophenes, which is advantageous for providing single-use or disposable compositions such as disinfecting wipes.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
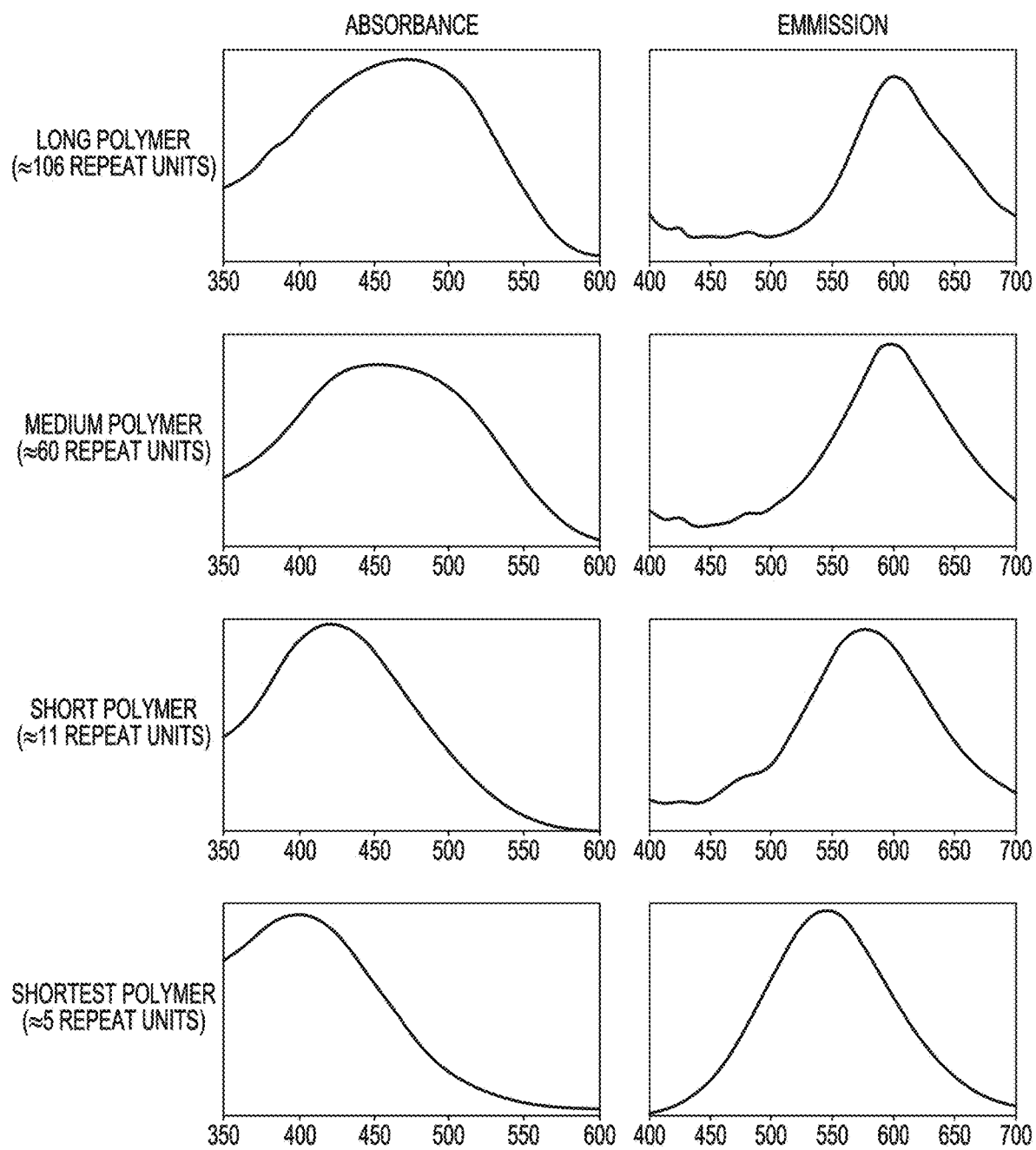
FIG. 1 shows the absorbance and emission spectra of P3 HT-Im polymer of four different sizes, large (≈106 repeat units); medium (≈60 repeat units), small (≈11 repeat units) and shortest (5 repeat units), the X axis of each chart shows the wavelength in (nm) and the Y axis corresponds to relative intensity, from low to high, of absorbance or emission.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%; 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. For each numerical value and range described herein, there is equally envisaged a corresponding numerical value which allows for a degree of variability, e.g., within 10%, within 5% or within 1% of the stated value or stated limit of a range, and a number which is "about" the stated value.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "heterocyclyl" as used herein refers to aromatic and non-aromatic ring compounds containing three or more ring members, of which one or more is a heteroatom such as, but not limited to, N, O, and S.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like, Examples of cyclic alkoxy include but are not limited to cyclopropyloxy, cyclobutyloxy, cyclopentyloxy, cyclohexyloxy, and the like, An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino; dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group, respectively, that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as (C$_a$-C$_b$)hydrocarbyl, wherein a and b are integers and mean having any of a to b number of carbon atoms. For example, (C$_1$-C$_4$)hydrocarbyl means the hydrocarbyl group can be methyl (C$_1$), ethyl (C$_2$), propyl (C$_3$), or butyl (C$_4$), and (C$_0$-C$_b$)hydrocarbyl means in certain embodiments there is no hydrocarbyl group.

The term "number-average molecular weight" (M$_n$) as used herein refers to the ordinary arithmetic mean of the molecular weight of individual molecules in a sample. It is defined as the total weight of all molecules in a sample divided by the total number of molecules in the sample. Experimentally, M$_n$ is determined by analyzing a sample divided into molecular weight fractions of species i having n$_i$ molecules of molecular weight M$_1$ through the formula M$_n$=ΣM$_i$n$_i$/Σn$_i$. The M$_n$ can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers to M$_w$, which is equal to ΣM$_i^2$n$_i$/ΣM$_i$n$_i$, where n$_i$ is the number of molecules of molecular weight M$_i$. In various examples, the weight-average molecular weight can be determined using light scattering, small angle neutron scattering, X-ray scattering, and sedimentation velocity.

The term "oligomer" as used herein refers to a molecule having an intermediate relative molecular mass, the structure of which essentially includes a small plurality of units derived, actually or conceptually, from molecules of lower relative molecular mass. A molecule having an intermediate relative mass can be a molecule that has properties that vary with the removal of one or a few of the units. The variation in the properties that results from the removal of the one of more units can be a significant variation.

The term "solvent" as used herein refers to a liquid that can dissolve a solid, liquid, or gas. Non-limiting examples of solvents are silicones, organic compounds, water, alcohols, ionic liquids, and supercritical fluids.

Herein, when it is designated that a variable in the structure can be "a bond," the variable can represent a direct bond between the two groups shown as linked to that variable, such as a single bond.

As used herein, the term "polymer" refers to a molecule having at least one repeating unit and can include copolymers.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$, or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate.

The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

The polymers described herein can terminate in any suitable way. In some embodiments, the polymers can terminate with an end group or terminal group that is independently chosen from a suitable polymerization initiator, —H, —OH, a substituted or unsubstituted ($C_1$-$C_{20}$) hydrocarbyl (e.g., ($C_1$-$C_{10}$)alkyl or ($C_6$-$C_{20}$)aryl) interrupted with 0, 1, 2, or 3 groups independently chosen from —O—, substituted or unsubstituted —NH—, and —S—, a poly (substituted or unsubstituted ($C_1$-$C_{20}$)hydrocarbyloxy), and a poly(substituted or unsubstituted ($C_1$-$C_{20}$)hydrocarbylamino).

Polythiophene

The present disclosure provides a polythiophene polymer having the structure:

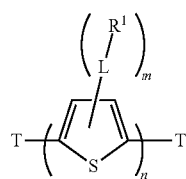

wherein
$R^1$ is

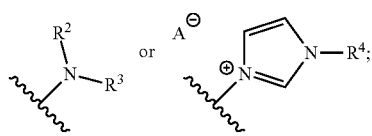

each of $R^2$ and $R^3$ is independently $C_1$-$C_6$ alkyl or $R^2$ and $R^3$ taken together are linked $C_2$-$C_5$ alkyl which forms a 3 to 6-membered saturated heterocyclic ring together with the nitrogen at which they attach;

$R^4$ is $C_1$-$C_6$ alkyl;

A is a counterion;

L is a divalent $C_1$-$C_{20}$ alkyl linker, optionally interrupted by 1, 2 or 3 oxygen, sulfur or nitrogen atoms;

T is a terminal group;

m is 1-2;

n is 5-14 or 30 to 120;

the polymer mixture has a number average molecular weight (Mn) from 1,000 to 4,000 or 10,000 to 40,000; and the polymer mixture has a polydispersity index (PDI) from 1 to 1.3.

In some embodiments the polythiophene is a polymer or oligomer having the following structure:

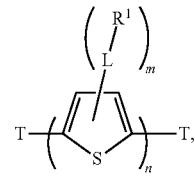

wherein m is 1 or 2;

n is 1 to 300;

L is a substituted or unsubstituted ($C_1$-$C_{20}$)hydrocarbylene interrupted with 0, 1, 2, or 3 groups that are independently chosen from —O—, —S—, and —NH—;

T is a terminal group; and $R^1$ is an ionic substituent optionally complexed with a counterion. The ionic substituent can be a quaternary ammonium salt, cationic heterocyclic group such as an N-alkyl imidazolium.

In various embodiments of the polythiophene, the number average molecular weight (Mn) is 20,000 to 40,000, n is 50 to 110, and the polydispersity index (PDI) is from 1 to 1.25.

In various embodiments of the polythiophene, the number average molecular weight (Mn) can be between 10,000 to 40,000. In various further embodiments, number average molecular weight (Mn) can be between 10,000 to 15,000, 10,000 to 20,000, 10,000 to 25,000, 10,000 to 30,000, 10,000 to 35,000, 10,000 to 40,000, 20,000 to 25,000, 20,000 to 30,000, 20,000 to 35,000, 20,000 to 40,000. The number average molecular weight (Mn) can be greater than or about, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000 or greater. In various embodiments, the number average molecular weight (Mn) can be less than 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000. In various embodiments, the number average molecular weight (Mn) can be between 1,000 to 2,000, 1,000 to 2,500, 1,000 to 3,000, 1,000 to 3,500, 2,000 to 2,500, 2,000 to 3,000, or 2,000 to 3,500.

In various embodiments, m is 1. The polythiophene polymer can have the structure:

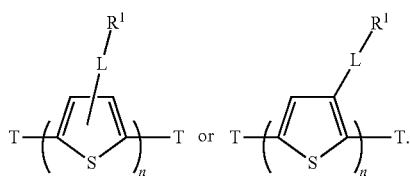

For example, in various embodiments, each thiophene is substituted with a single L-R$^1$ group but the regiochemistry of the substituent can vary from one thiophene to the next or can be substantially regiospecific.

In various embodiments of the polythiophene, n is greater than, or about, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 or at least 110. In various embodiments of the polythiophene, n is less than 7, 8, 9, 10, 11, 12, 13, 14, 15, 16, 17, 18, 19, 20, 21, 22, 23, 24, 25. In various embodiments of the polythiophene, n is not one or more of 15, 16, 17, 18, 19, 20, 21, 22, 23, 24, 25, 26, 27, 28, 29 and 30.

In various embodiments of the polythiophene, the variable n can be chosen from any integer between 2 and 14 and between 20 and 110, for example n can be 5, 11, 60 or 106. For example, n can be any integer in the range of 2-15, 4-12, 5-11, 8-14, 9-14, 10-14, 11-14, 8-12, 9-12, 10-12, 20-110, 30-110, 40-110, 50-110, 60-110, 20-106, 30-106, 40-106, 50-106, 60-106, 30-70, 40-70, 50-70, 55-65, 60-70, 30-80, 40-80, 50-80, 60-80, 70-120, 80-120, 90-120, 100-120, 70-110, 80-110, 90-110 or 100-110. In some embodiments, the polythiophene may some strands having n in the range of 2-15, 4-12, 5-11, 8-14, 9-14, 10-14, 11-14, 8-12, 9-12 or 10-12 and also some strands having n in the range of 50-110, 60-110, 20-106, 30-106, 40-106, 50-106, 60-106, 30-70, 40-70, 50-70, 55-65, 60-70, 30-80, 40-80, 50-80, 60-80, 70-120, 80-120, 90-120, 100-120, 70-110, 80-110, 90-110 or 100-110.

In various embodiments of the polythiophene, the polydispersity index (PDI) is less than or about 1.25, 1.24, 1.23, 1.22, 1.21, 1.20, 1.19, 1.18, 1.17, 1.16, 1.15, 1.14, 1.13, 1.12, 1.11, 1.10, 1.09, 1.08, 1.07, 1.06 or less than or about 1.05. In various embodiments, the PDI may be greater than 1.01, 1.02, 1.03, 1.04, 1.05, 1.06, 1.07, 1.08, 1.09, 1.10, 1.11, 1.12, 1.13, 1.14, 1.15, 1.16, 1.17, 1.18 or greater than 1.19.

In various embodiments of the polythiophene, R$^1$ is

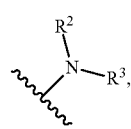

which may be optionally protonated which results in a positively charged species paired with a counterion A$^-$. R$^2$ and R$^3$ can each independently be methyl, ethyl, propyl, butyl, pentyl or hexyl. Taken together R$^2$ and R$^3$ can result in a pyrrolidine or a piperidine. In various embodiments, R$^2$ and R$^3$ is each ethyl.

In various embodiments of the polythiophene, R$^1$ is

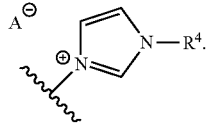

R$^4$ can be methyl, ethyl, propyl, butyl, pentyl or hexyl. In various embodiments, R$^1$ is an optionally substituted N-methylimidazolium. R$^1$ can be

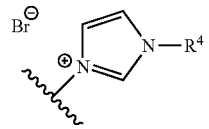

and in various embodiments is

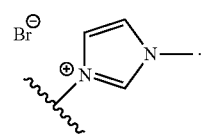

In various embodiments of the polythiophene, L can be an unsubstituted (C$_1$-C$_{10}$)alkylene and, in yet further embodiments, L is a substituted or unsubstituted (C$_6$)hexylene. In various embodiments of the polythiophene, L is a divalent methyl, ethyl, propyl, butyl, pentyl or hexyl. In various embodiments, L is hexyl.

In various embodiments, the polythiophene has the structure:

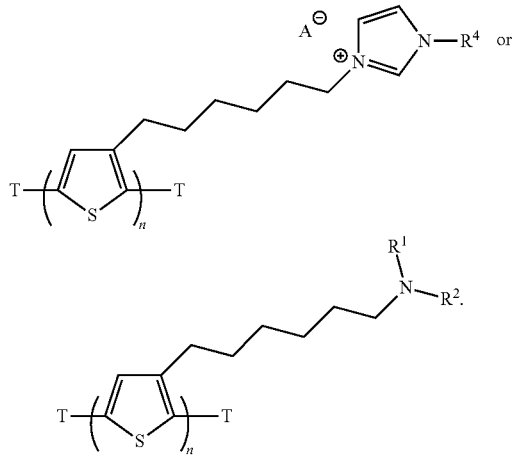

In some embodiments, the polythiophene has the structure:

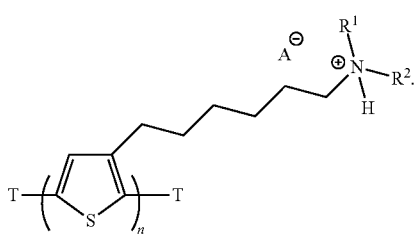

In further embodiments, the polythiophene has the structure:

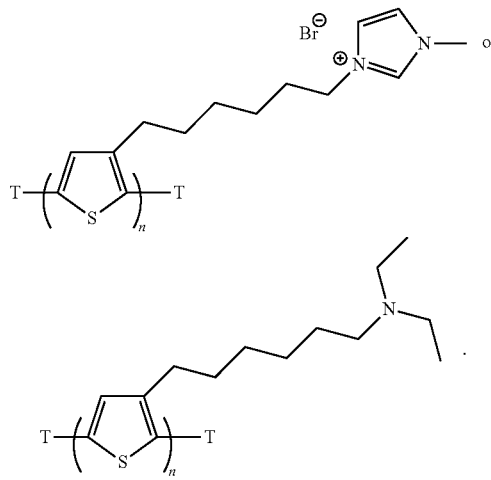

In various embodiments of the polythiophene, T can be independently chosen from —H and $(C_1-C_{10})$hydrocarbyl. In various embodiments, T is –H. In various embodiments, T is methyl, ethyl, propyl, butyl, pentyl or hexyl.

In various embodiments of the polythiophene, the counterion can be a halide such as chloride, bromide and iodide. In various embodiments, the counterion can be a sulfate, a phosphate, a sulfite, a phosphite, a carbonate, or a combination thereof. The counterion can be a combination of one or more counterions.

In various embodiments, the polythiophene has antimicrobial properties.

Antimicrobial Substrate

The present disclosure provides an antimicrobial substrate. The antimicrobial substrate can include one or more polythiophenes, such as any of the polythiophenes described herein. The antimicrobial substrate also includes a substrate.

For example, the present disclosure provides an antimicrobial substrate, comprising a substrate and a polythiophene having the structure

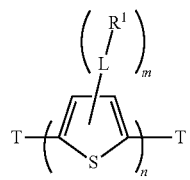

wherein
$R^1$ is

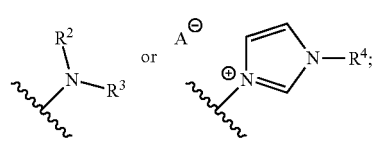

each of $R^2$ and $R^3$ is independently $C_1-C_6$ alkyl or $R^2$ and $R^3$ taken together are linked $C_2-C_5$ alkyl which forms a 3 to 6-membered saturated heterocyclic ring together with the nitrogen at which they attach;

$R^4$ is $C_1-C_6$ alkyl;
A is a counterion;
L is a divalent $C_1-C_{20}$ alkyl linker, optionally interrupted by 1, 2 or 3 oxygen, sulfur or nitrogen atoms;
T is a terminal group;
m is 1-2;
n is 30 to 120;
the polythiophene has a number average molecular weight (Mn) from 10,000 to 40,000; and
the polythiophene has a polydispersity index (PDI) is from 1 to 1.3.

In various embodiments of the antimicrobial substrate, the number average molecular weight (Mn) is 20,000 to 40,000, n is 50 to 110, and the polydispersity index (PDI) is from 1 to 1.25.

For example, the present disclosure provides an antimicrobial substrate, comprising a substrate and a polythiophene having the structure

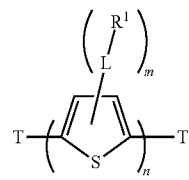

wherein
$R^1$ is

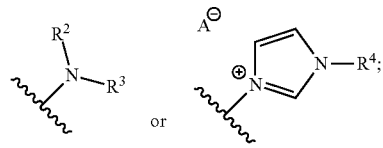

each of $R^2$ and $R^3$ is independently $C_1-C_6$ alkyl or $R^2$ and $R^3$ taken together are linked $C_2-C_5$ alkyl which forms a 3 to 6-membered saturated heterocyclic ring together with the nitrogen at which they attach;
$R^4$ is $C_1-C_6$ alkyl;
A is a counterion;
L is a divalent $C_1-C_{20}$ alkyl linker, optionally interrupted by 1, 2 or 3 oxygen, sulfur or nitrogen atoms;
T is a terminal group;
m is 1-2;
n is 2 to 14;
the polythiophene has a number average molecular weight (Mn) from 1,000 to 4,000; and
the polythiophene has a polydispersity index (PDI) is from 1 to 1.3.

In various embodiments of the antimicrobial substrate, the number average molecular weight (Mn) is 1,500 to 3,000, n is 6 to 12, and the polydispersity index (PDI) is from 1 to 1.25.

In various embodiments, the antimicrobial substrate is configured to retain the polythiophene antimicrobial agent and can, for example, comprise polythiophenes having n is larger than 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 or larger than 110. As a further example, the substrate configured to retain the antimicrobial polythiophene may comprise polythiophenes having a cationic $R^1$ group such as a substituted or unsubstituted imidazolium. As a yet further example, the substrate configured to retain the antimicrobial polythiophene may comprise polythiophenes having a number average molecular weight (Mn) between 10,000 to 15,000, 10,000 to 20,000, 10,000 to 25,000, 10,000 to 30,000, 10,000 to 35,000, 10,000 to 40,000, 20,000 to 25,000, 20,000 to 30,000, 20,000 to 35,000, 20,000 to 40,000, or a number average molecular weight (Mn) greater than or about 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000 or greater. In various embodiments, the polythiophenes are retained after washing with one or more of water, detergent and organic solvent.

In various embodiments, the antimicrobial substrate is configured to deposit a residue of antimicrobial polythiophenes and can, in some embodiments, comprise polythiophenes having n is less than 10, 11, 12, 13, 14, 15, 16, 17, 18, 19 or 20. As a further example, the substrate configured to deposit a residue of polythiophenes and may, e.g., comprise polythiophenes for which $R^1$ is a neutral group or in equilibrium with a neutral group, e.g., $R^1$ is

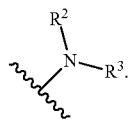

As a yet further example, the substrate configured to retain the antimicrobial polythiophene may comprise polythiophenes having a number average molecular weight (Mn) between 1,000 to 2,000, 1,000 to 2,500, 1,000 to 3,000, 1,000 to 3,500, 2,000 to 2,500, 2,000 to 3,000, or 2,000 to 3,500. In various embodiments, the polythiophenes can be readily removed from the substrate or the residue washed off a treated surface by treatment with base, such as triethylamine.

In various embodiments of the antimicrobial substrate, the number average molecular weight (Mn) can be between 10,000 to 40,000. In various further embodiments, number average molecular weight (Mn) can be between 10,000 to 15,000, 10,000 to 20,000, 10,000 to 25,000, 10,000 to 30,000, 10,000 to 35,000, 10,000 to 40,000, 20,000 to 25,000, 20,000 to 30,000, 20,000 to 35,000, 20,000 to 40,000. The number average molecular weight (Mn) can be greater than or about, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000 or greater. In various embodiments, the number average molecular weight (Mn) can be less than 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000. In various embodiments, the number average molecular weight (Mn) can be between 1,000 to 2,000, 1,000 to 2,500, 1,000 to 3,000, 1,000 to 3,500, 2,000 to 2,500, 2,000 to 3,000, or 2,000 to 3,500.

In various embodiments of the antimicrobial substrate, the polythiophene has m is 1. The polythiophene polymer can have the structure:

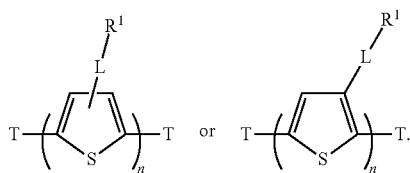

For example, in various embodiments, each thiophene is substituted with a single L-$R^1$ group but the regiochemistry of the substituent can vary from one thiophene to the next or can be substantially regiospecific.

In various embodiments of the antimicrobial substrate, n is greater than, or about, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 or at least 110. In various embodiments of the antimicrobial substrate, n is less than 7, 8, 9, 10, 11, 12, 13, 14, 15, 16, 17, 18, 19, 20, 21, 22, 23, 24, 25. In various embodiments of the antimicrobial substrate, n is not one or more of 15, 16, 17, 18, 19, 20, 21, 22, 23, 24, 25, 26, 27, 28, 29 and 30.

In various embodiments of the antimicrobial substrate, the variable n can be chosen from any integer between 2 and 14 and between 20 and 110, for example n can be 5, 11, 60 or 106. For example, n can be any integer in the range of 2-15, 4-12, 5-11, 8-14, 9-14, 10-14, 11-14, 8-12, 9-12, 10-12, 20-110, 30-110, 40-110, 50-110, 60-110, 20-106, 30-106, 40-106, 50-106, 60-106, 30-70, 40-70, 50-70, 55-65, 60-70, 30-80, 40-80, 50-80, 60-80, 70-120, 80-120, 90-120, 100-120, 70-110, 80-110, 90-110 or 100-110. In some embodiments, the polythiophene may some strands having n in the range of 2-15, 4-12, 5-11, 8-14, 9-14, 10-14, 11-14, 8-12, 9-12 or 10-12 and also some strands having n in the range of 50-110, 60-110, 20-106, 30-106, 40-106, 50-106, 60-106, 30-70, 40-70, 50-70, 55-65, 60-70, 30-80, 40-80, 50-80, 60-80, 70-120, 80-120, 90-120, 100-120, 70-110, 80-110, 90-110 or 100-110.

In various embodiments of the antimicrobial substrate, the polydispersity index (PDI) is less than or about 1.25, 1.24, 1.23, 1.22, 1.21, 1.20, 1.19, 1.18, 1.17, 1.16, 1.15, 1.14, 1.13, 1.12, 1.11, 1.10, 1.09, 1.08, 1.07, 1.06 or less than or about 1.05. In various embodiments, the PDI may be greater than 1.01, 1.02, 1.03, 1.04, 1.05, 1.06, 1.07, 1.08, 1.09, 1.10, 1.11, 1.12, 1.13, 1.14, 1.15, 1.16, 1.17, 1.18 or greater than 1.19.

In various embodiments of the antimicrobial substrate, $R^1$ is

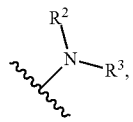

which may be optionally protonated which results in a positively charged species paired with a counterion $A^-$. $R^2$ and $R^3$ can each independently be methyl, ethyl, propyl, butyl, pentyl or hexyl. Taken together $R^2$ and $R^3$ can result in a pyrrolidine or a piperidine. In various embodiments, $R^2$ and $R^3$ is each ethyl.

In various embodiments of the antimicrobial substrate, $R^1$ is

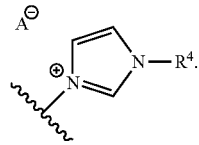

$R^4$ can be methyl, ethyl, propyl, butyl, pentyl or hexyl. In various embodiments, $R^1$ is an optionally substituted N-methylimidazolium. $R^1$ can be

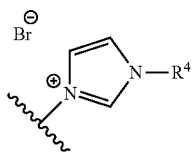

and in various embodiments is

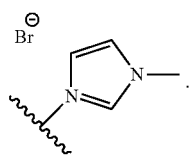

In various embodiments of the antimicrobial substrate, L can be an unsubstituted $(C_1-C_{10})$alkylene and, in yet further embodiments, L is a substituted or unsubstituted $(C_6)$hexylene. In various embodiments of the antimicrobial substrate, L is a divalent methyl, ethyl, propyl, butyl, pentyl or hexyl. In various embodiments, L is hexyl.

In various embodiments of the antimicrobial substrate, the polythiophene has the structure:

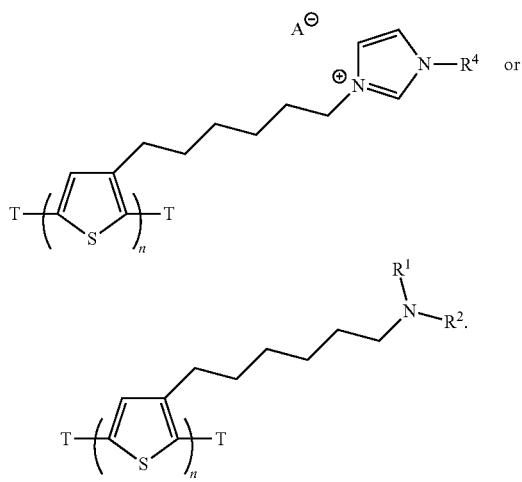

In some embodiments of the antimicrobial substrate, the polythiophene has the structure:

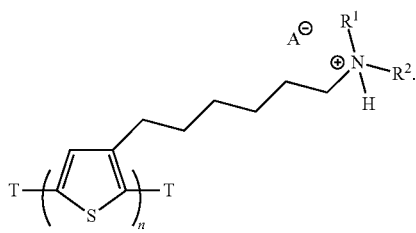

In further embodiments of the antimicrobial substrate, the polythiophene has the structure:

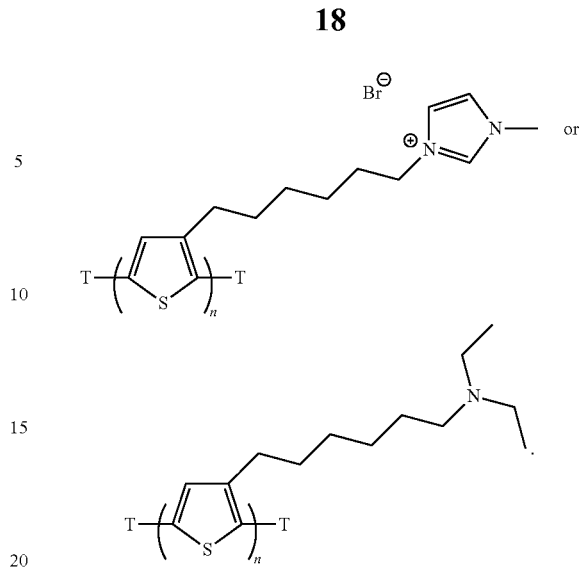

In various embodiments of the antimicrobial substrate, T can be independently chosen from —H and $(C_1-C_{10})$hydrocarbyl. In various embodiments, T is —H. In various embodiments, T is methyl, ethyl, propyl, butyl, pentyl or hexyl.

In various embodiments of the antimicrobial substrate, the counterion can be a halide such as chloride, bromide and iodide. In various embodiments, the counterion can be a sulfate, a phosphate, a sulfite, a phosphite, a carbonate, or a combination thereof. The counterion can be a combination of one or more counterions.

In various embodiments, the antimicrobial substrate, the substrate is a wipe, a tissue, a bandage, a medical device, surgical instrument, tubing, a catheter, warfighter machinery, a sponge, a textile, a diaper, a counter-top, a food preparation surface, a wound dressing, a dressing for surgical incisions, a keyboard surface, a packing for wounds, a packing for surgical incisions, a nasal packing or a feminine care product, or a combination thereof.

In various embodiments of the antimicrobial substrate, the substrate is a wipe.

In various embodiments, the antimicrobial substrate can be configured to be reusable, for example, a reusable wipe, tissue, bandage, medical device, surgical instrument, tubing, catheter, warfighter machinery, sponge, textile, diaper, counter-top, food preparation surface, wound dressing, dressing for surgical incisions, keyboard surface, packing for wounds, packing for surgical incisions, nasal packing or feminine care product. Any such reusable antimicrobial substrate may have embedded antimicrobial polythiophenes retained therein. Such embedded antimicrobial polythiophenes can, in various embodiments, have n is larger than 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 or larger than 110. As a further example, the embedded antimicrobial polythiophene having a cationic $R^1$ group such as a substituted or unsubstituted imidazolium. As a yet further example, the embedded antimicrobial polythiophene can have a number average molecular weight (Mn) between 10,000 to 15,000, 10,000 to 20,000, 10,000 to 25,000, 10,000 to 30,000, 10,000 to 35,000, 10,000 to 40,000, 20,000 to 25,000, 20,000 to 30,000, 20,000 to 35,000, 20,000 to 40,000, or a number average molecular weight (Mn) greater than or about 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000 or greater. In various embodiments, the polythiophenes in a reusable antimicrobial substrate are retained after washing with one or more of water, detergent and organic solvent.

In further embodiments, the antimicrobial substrate can be any one or more of single use, disposable, and configured to function as a vehicle for providing disinfectant to an object, surface or area. For example, a single use, disposable and/or disinfectant-providing wipe, tissue, bandage, medical device, surgical instrument, tubing, catheter, warfighter machinery, sponge, textile, diaper, counter-top, food preparation surface, wound dressing, dressing for surgical incisions, keyboard surface, packing for wounds, packing for surgical incisions, nasal packing or feminine care product. Any such disposable antimicrobial substrate can, in various embodiments, be configured to deposit a residue of polythiophene. Such polythiophenes configured to be deposited can have, in various embodiments, n is less than 10, 11, 12, 13, 14, 15, 16, 17, 18, 19 or 20. As a further example, the substrate configured to deposit a residue of polythiophenes and may, e.g., comprise polythiophenes for which $R^1$ is a neutral group or in equilibrium with a neutral group, e.g., $R^1$ is

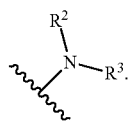

As a yet further example, the substrate configured to retain the antimicrobial polythiophene may comprise polythiophenes having a number average molecular weight (Mn) between 1,000 to 2,000, 1,000 to 2,500, 1,000 to 3,000, 1,000 to 3,500, 2,000 to 2,500, 2,000 to 3,000, or 2,000 to 3,500. In various embodiments, the polythiophenes can be readily removed from the substrate or the residue washed off a treated surface by treatment with base, such as triethylamine.

In various embodiments of the antimicrobial substrate, about 1 µg/cm³ to about 10 µg/cm³ of the antimicrobial substrate is the polythiophene. In some embodiments, about 0.5 µg/cm³ to about 20 µg/cm³ or about 0.1 µg/cm³ to about 100 µg/cm³ of the antimicrobial substrate is the polythiophene.

In various such embodiments, the antimicrobial substrate may be saturated with the polythiophene. Such substrates may in some embodiments additionally contain detergents and solubilizers.

In various embodiments of the antimicrobial substrate, the polythiophene provides a temporary antimicrobial coating on the substrate which is removable by treatment with one or more of water, organic solvent, base and detergent.

In various embodiments of the antimicrobial substrate, the polythiophene is embedded in the substrate and remains at a concentration of about from about 0.1 µg/cm³ to about 10 µg/cm³ after washing the antimicrobial substrate.

In various embodiments of the antimicrobial substrate, the polythiophene is deposited on a surface, object or area to be treated at a concentration of about from about 0.1 µg/cm³ to about 10 µg/cm³ after washing the antimicrobial substrate.

In various embodiments of the antimicrobial substrate, the polythiophene absorbs visible light. In various embodiments, the polythiophene can be configured to function as a passively photoactivated antimicrobial, e.g., by absorbing visible light to generate reactive oxygen species. Such antimicrobial substrates, in various embodiments, can comprise polythiophenes, which primary absorb light in the visible range. Such visible light optimized polythiophenes may, in some embodiments, have n is larger than 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 or larger than 110. As a yet further example, the visible light optimized polythiophene can have a number average molecular weight (Mn) between 10,000 to 15,000, 10,000 to 20,000, 10,000 to 25,000, 10,000 to 30,000, 10,000 to 35,000, 10,000 to 40,000, 20,000 to 25,000, 20,000 to 30,000, 20,000 to 35,000, 20,000 to 40,000, or a number average molecular weight (Mn) greater than or about 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000 or greater.

In various embodiments of the antimicrobial substrate, the polythiophene absorbs UV light, e.g., UVA, UVB and/or UVC. In various embodiments, the polythiophene can be configured to function as an actively photoactivated antimicrobial, e.g., by absorbing visible light to generate reactive oxygen species. Such antimicrobial substrates can, in various embodiments, can comprise polythiophenes which primary absorb light in the UV range, rather than in the visible range. Such polythiophene can have, in various embodiments, n is less than 10, 11, 12, 13, 14, 15, 16, 17, 18, 19 or 20. As a further example, the UV optimized polythiophene may have a number average molecular weight (Mn) between 1,000 to 2,000, 1,000 to 2,500, 1,000 to 3,000, 1,000 to 3,500, 2,000 to 2,500, 2,000 to 3,000, or 2,000 to 3,500.

In various further embodiments, the antimicrobial substrate may be configured to respond to the preferred light source by adjusting polymer size (e.g., the n value or number average molecule weight) and, also, by complexation with micelle forming agents and counterions (e.g., SDS and other detergents), by complexation with polysaccharides or by formulation as a hydrogel.

In various embodiments of the antimicrobial substrate, the substrate is a polysaccharide.

In various embodiments of the antimicrobial substrate, the polysaccharide is alginate, carboxymethyl amylose or carboxymethyl cellulose.

In various embodiments, the antimicrobial substrate is in the form of a hydrogel. In some embodiments, the antimicrobial substrate is in the form of an alginate hydrogel.

In various embodiments the antimicrobial substrate further comprising at least one of a detergent, a calcium salt and a copper salt.

The substrate can be any suitable substrate that has antimicrobial properties when it includes the polythiophenes. As used herein, the term "antimicrobial" refers to the ability to inhibit growth and/or kill bacterium, for example Gram-positive and Gram-negative bacteria. The substrate can be any suitable substrate where it would be advantageous to have at least one surface having antimicrobial properties.

The polythiophenes can be non-leachably bound to the substrate. In various embodiments, the antimicrobial compound is leachably bound to the substrate. When the antimicrobial compound is non-leachably bound to the substrate, wiping a surface with the antimicrobial substrate can lead to substantially no transfer of the antimicrobial compound to the new surface. In some embodiments, this transfer can be monitored by observing the fluorescence of the antimicrobial compound.

The polythiophene can be in contact with at least one surface of the substrate. The polythiophene can be substantially uniformly distributed on the substrate. One or more layers can separate the polythiophene from the substrate.

The antimicrobial substrate can exhibit antimicrobial properties. For example, the antimicrobial substrate can prevent or inhibit growth of at least one of Gram-positive *Staphylococcus aureus*, Gram-negative *Pseudomonas aeruginosa*, and *Escherichia coli*. The antimicrobial properties of the antimicrobial substrate can exceed the antimicrobial properties of a corresponding substrate without the antimicrobial compound. The antimicrobial substrate can exhibit antimicrobial properties in a non-aqueous environment.

In some embodiments the substrate is in a sensor and, in some embodiments, the present disclosure provides a sensor comprising a polythiophene described herein.

In some embodiments the substrate is in a medication and, in some embodiments, the present disclosure provides a medication comprising a polythiophene described herein.

In various embodiments, the polythiophene polymer or oligomer can have an absorption or emission spectrum that depends not only on the length of the polymer or oligomer but also on the chemical environment surrounding the polymer or oligomer, such as the types of molecules in the environment and the concentration of molecules in the environment. In various embodiments, the polythiophene polymer or oligomer can have antimicrobial properties. Various embodiments provide sensors, drug delivery devices, or hydrogels incorporating the polythiophene polymer or oligomer.

The present invention also includes modified substrates and other compositions which are not antimicrobial. Such compositions can be useful due to its absorption or emission properties, its ability to associate with bacteria, its ability to organize cellular debris, or, e.g., as a sensor or drug delivery agent.

Method of Disinfecting

The present disclosure also provides a method of inactivating a microorganism. The method can include contacting the microorganism with an effective amount or concentration of a polythiophenes, such as any one or more polythiophenes described herein.

In various embodiments, the present disclosure provides a method of disinfecting, comprising treating a surface with a disinfectant composition which comprises a carrier and a polythiophene having the structure

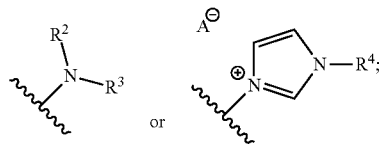

wherein
R$^1$ is

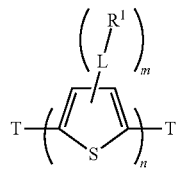

each of R$^2$ and R$^3$ is independently C$_1$-C$_6$ alkyl or R$^2$ and R$^3$ taken together are linked C$_2$-C$_5$ alkyl which forms a 3 to 6-membered saturated heterocyclic ring together with the nitrogen at which they attach;

R$^4$ is C$_1$-C$_6$ alkyl;

A is a counterion;

L is a divalent C$_1$-C$_{20}$ alkyl linker, optionally interrupted by 1, 2 or 3 oxygen, sulfur or nitrogen atoms;

T is a terminal group;

m is 1-2;

n is 5-14 or 30 to 120;

the polythiophene has a number average molecular weight (Mn) is from 1,000 to 4,000 or 10,000 to 40,000;

and the polythiophene has a polydispersity index (PDI) is from 1 to 1.3.

In various embodiments of the method, area is treated with the disinfectant composition via a spray, a lotion, a dip, a bath, or by contact with a substrate saturated with the disinfectant composition. Additionally, the disinfectant composition is envisaged to suitable incorporate all of the embodiments set forth for the antimicrobial substrate described herein, differing in that the substrate is replaced with a carrier. In various embodiments, the carrier can be a fluid, e.g., a liquid fluid. In various embodiments, the polythiophenes are dissolved in the carrier. In various embodiments, the polythiophenes are suspended in the carrier.

In various embodiments of the method, the carrier comprises water. In various further embodiments, the carrier comprises one or more of an alcohol or organic solvent. In some embodiments, the alcohol is ethanol. The carrier can further comprise detergents, solubilizers, chelators, a buffer system and colorants.

In various embodiments, the carrier can have be at a neutral pH, an acidic pH or a basic pH. For example, the carrier can have a pH of 6-8. In various embodiments, the carrier has a pH greater than 8 or less than 6.

In various embodiments, the disinfectant composition is configured to deposit a residue of polythiophenes on the treated object, area or surface.

In further embodiments, the disinfectant composition comprises polythiophenes having n is less than 10, 11, 12, 13, 14, 15, 16, 17, 18, 19 or 20. As a further example, the substrate configured to deposit a residue of polythiophenes and may, e.g., comprise polythiophenes for which R$^1$ is a neutral group or in equilibrium with a neutral group, e.g., R$^1$ is

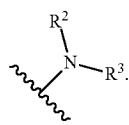

As a yet further example, the substrate configured to retain the antimicrobial polythiophene may comprise polythiophenes having a number average molecular weight (Mn) between 1,000 to 2,000, 1,000 to 2,500, 1,000 to 3,000, 1,000 to 3,500, 2,000 to 2,500, 2,000 to 3,000, or 2,000 to 3,500. In various embodiments, the polythiophenes can be readily removed from the substrate or the residue washed off a treated surface by treatment with base, such as triethylamine.

In various embodiments, the disinfect composition is formulated to provide polythiophenes which are long-acting. Such long-acting polythiophenes can, in various embodiments, have n is larger than 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 or larger than 110. As a further example, the embedded antimicrobial polythiophene having a cationic $R^1$ group such as a substituted or unsubstituted imidazolium. As a yet further example, the embedded antimicrobial polythiophene can have a number average molecular weight (Mn) between 10,000 to 15,000, 10,000 to 20,000, 10,000 to 25,000, 10,000 to 30,000, 10,000 to 35,000, 10,000 to 40,000, 20,000 to 25,000, 20,000 to 30,000, 20,000 to 35,000, 20,000 to 40,000, or a number average molecular weight (Mn) greater than or about 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000 or 45,000 or greater. In various embodiments, the polythiophenes in a reusable antimicrobial substrate are retained after washing with one or more of water, detergent and organic solvent.

The microorganism to be treated can be any microorganism that can be inactivated by one or more polythiophenes described herein. For example, the microorganism can include at least one of a bacterium, virus, fungus, mold, slime mold, algae, and yeast.

In various embodiments, the present disclosure provides a method of inactivating bacteria. The method can include contacting the bacteria with an effective amount or concentration of a polythiophenes described herein.

In various embodiments, the present disclosure also provides a method of disinfecting an object. The method can include contacting the object with an effective amount or concentration of any one or more polythiophenes described herein.

The object can be any suitable object that can be at least partially disinfected by contacting with one or more polythiophenes described herein.

In various embodiments, the present disclosure provides a method of treating a substrate. The method can include contacting the substrate with one or more polythiophenes described herein.

The contacted substrate can have antimicrobial properties. The antimicrobial properties can include prevention of growth of at least one of Gram-positive *Staphylococcus aureus*, Gram-negative *Pseudomonas aeruginosa*, and *Escherichia coli*. The antimicrobial properties of the contacted substrate can exceed the antimicrobial properties of the substrate prior to the contacting. The contacted substrate can have antimicrobial properties in a non-aqueous environment.

The substrate can be any suitable substrate that can exhibit antimicrobial properties after being contacted with the one or more polythiophenes. The substrate can be at least one of a wipe, a tissue, a bandage, a medical device, surgical instrument, warfighter machinery, a sponge, a textile, a diaper, a counter-top, a food preparation surface, a wound dressing, a dressing for surgical incisions, a keyboard surface, a packing for wounds, a packing for surgical incisions, a nasal packing, and a feminine care product.

The contacting can be performed in any suitable way. The contact can be performed by at least one of foamed applicators, cotton swabs, saturated swab sticks, saturated wipes, aerosols, sprays, brushes, and dips. In various embodiments, the contacting is accomplished by at least on of an aerosol spray and spray. For example, the antimicrobial compound may be mixed with an aerosol propellant (e.g., dichlorodifluoromethane, trichlorofluoromethane, dichlorotetrafluoroethane, carbon dioxide or other suitable gas).

EXAMPLES

Various embodiments of the present disclosure can be better understood by reference to the following Examples which are offered by way of illustration. The present disclosure is not limited to the Examples given herein.

Cell Growth and Preparation

*Bacillus atrophaeus* (ATCC No. 9372) vegetative cells were generated from dilute spore stocks suspended in sterile de-ionized water stored at 4° C. 2 µL of spore solution was then added to 50 mL of Bacto™ Tryptic Soy Broth (TSB) and incubated at 30° C. between 16-18 h while shaking at 240 rpm. *Escherichia coli* slants were generated from 20% glycerol suspended stocks stored at −80° C. *E. coli* was inoculated in TSB from the slant stocks using the same growth conditions as *B. atrophaeus*. 1 mL of *B. atrophaeus* or *E. coli* cell culture was added to 1.5 mL Eppendorf tubes and washed 5 times by centrifugation in 0.85% NaCl solution. Centrifugation was carried out at ~4.5 k rpm for 5 minutes each. Pellets were resuspended in sterile 0.85% NaCl solution and cell concentration was calculated using a hemocytometer.

Viability Testing

A total volume of 1 mL in transparent 1.5-dram vials (photolysis) and amber dram vials (dark) was used for each sample undergoing viability testing. Cells were diluted in 0.85% NaCl buffer then exposed to concentrations of 1 µg/mL and 10 µg/mL of P3 HT-T or P3 HT-Im from 1 mg/mL stock solutions. Concentrations of approximately $10^7$ cells/mL were used for all viability tests. Samples were then exposed to blue-violet visible light ($\lambda_{max}$ approx. 420 nm, power 2.28±0.03 mW/cm²) in a photochamber (dose approx. 8.2 J/cm²), or dark conditions for 1 h. After exposure, 1 µL of dead stain (propidium iodide) and live stain (SYTO 21™ or SYTO 13™) were used to dye each sample over a period of 30 minutes. Stains were varied due to accessibility and accounted for in data analysis. Dark samples were prepared entirely under low light conditions in a dark room to reduce the potential for photolysis to occur from natural light as the polymers absorb strongly in the visible range.

Samples were then run on a BD Accuri™ C6 flow cytometer to determine percent live or dead in each sample. FL1 detectors at 530±15 nm and FL3 at wavelength>670 nm were used to assess live and dead fluorescence respectively. Thresholds were set at FSC 80,000 and FLH-1 250 with fluidics set at 14 µL/min and core diameter of 10 µm. A total of 10,000 events was collected per sample. 3 samples for each concentration of polymer under photolysis were tested per experiment. FlowJO™ software was used to analyze data and develop live dead gating schemes for each bacterial species.

Transmission Electron Microscopy of Bacterial Species

To visualize the morphologies of damaged bacteria, TEM images of bacteria were obtained on glow discharged (Harrick Plasma Cleaner) 6-8 nm carbon films on 400-mesh copper grids (Ted Pella, CA). The samples were prepared in 0.85% NaCl solution with ~$10^7$ cells/mL in 1.5-dram vials and exposed to concentrations of 10 µg/mL of medium sized P3 HT-T and P3 HT-Im. Samples were either irradiated for 1 h in blue-violet light or left under dark conditions for 1 h. Controls were prepared as ~$10^7$ cells/mL in NaCl solution and left in dark conditions. After exposure 5 uL of sample were dropped on to TEM grids and left to dry for half an hour. Dark samples were kept in a concealed location to prevent natural light from reaching them during the drying period. TEM images were taken using a TEM instrument (H-7500, Hitachi, Japan) equipped with an AMT XR60 camera (AMT Imagining) at an accelerating voltage of 80 kV at 15000-fold magnification in high contrast mode.

Statistical Analysis

Samples were prepared in sets of 3, aside from negative controls which were taken as 1 sample. The average of 3 samples are presented with standard deviation shown as the error. To report significance of findings, excel was used to carry out T-Tests between light and dark samples within the same polymer class.

Synthesis of P3 HT-Br

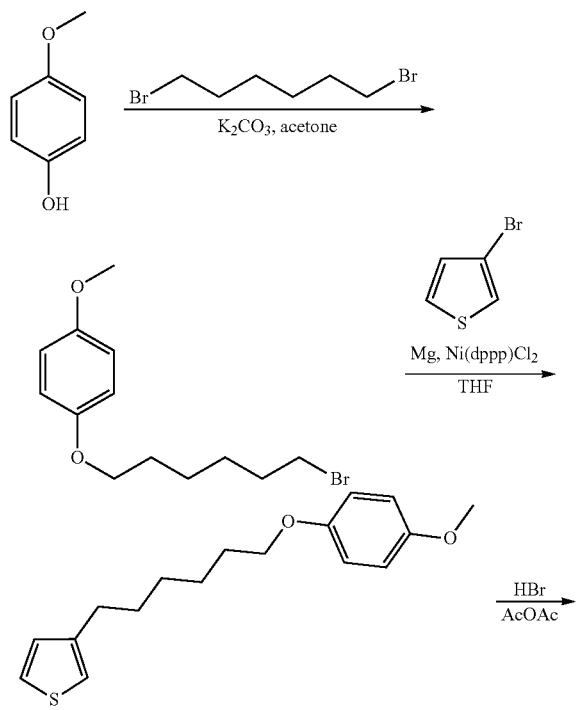

Scheme 1. Synthesis route of P3HT-Br

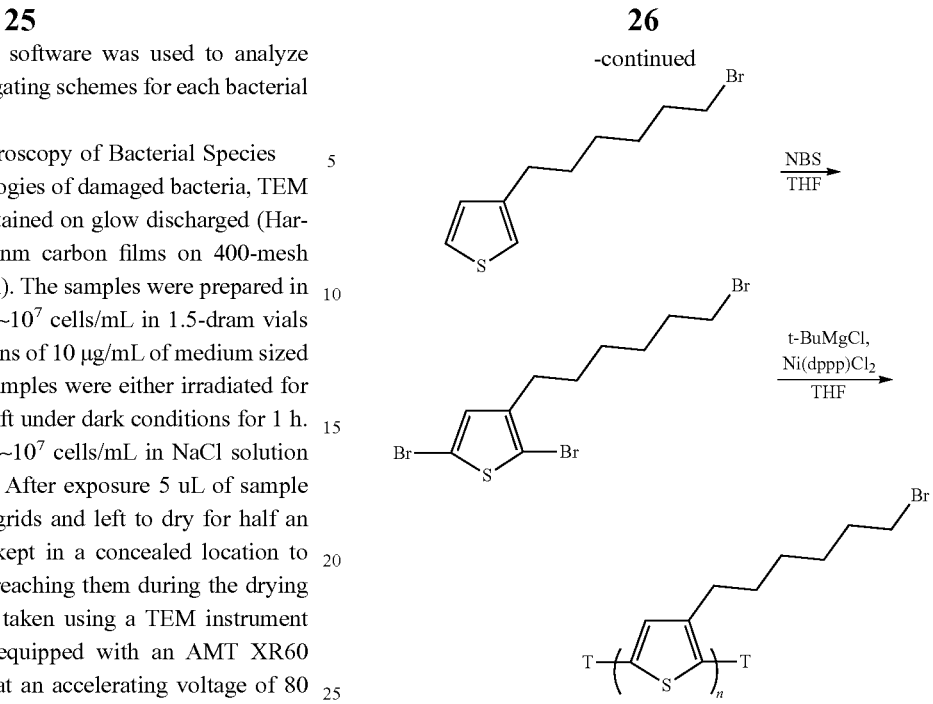

P3 HT-Br was prepared according to Scheme 1, and polymerization conditions were adjusted to provide product at various sizes. This general approach for preparation of P3 HT-Br is based on a modified version of a method described in Huang et al. (2017) Selective Imaging and Inactivation of Bacteria over Mammalian Cells by Imidazolium-Substituted Polythiophene. Chem. Mater. 29, 6389-6395, which is herein incorporated by reference in its entirety. The method of Huang et al. only provided P3 HT-Br having an Mn of 5000 g/mol and a polydispersity index (PDI) of 1.39. Similar P3 HT-Br is also described in U.S. Pat. No. 9,750,250, which is also incorporated by reference herewith. The Grignard metathesis (GRIM) step herein differs in that it was modified to provide polymerization conditions which resulted in new sizes of P3 HT-Br which were not obtainable by previously described methods. For example, the P3 HT-Br described herein has a lower PDI value than the prior P3 HT-Br which has a PDI of greater than 1.35, and also the P3 HT-Br described herein has a lower molecular weight (e.g., as in P3 HT-Br S) or higher molecular weight (e.g., P3 HT-Br M and P3 HT-Br L). The new differing chain lengths of polythiophene result in polythiophenes having properties, described in detail below, that were not predictable. Chain length was successfully controlled at the Grignard metathesis (GRIM) stage of the preparation of P3 HT-Br. The molecular weight and polydispersity of P3 HT-Br were determined via Gel Permeation Chromatography (GPC) measurements, which are summarized in Table 1.

TABLE 1

GPC data of 3 batches of P3HT-Br

| Polymer | Mn (Da) | Mw(Da) | PDI | DP |
| --- | --- | --- | --- | --- |
| P3HT-Br S | 2711 | 3277 | 1.21 | 11 |
| P3HT-Br M | 14791 | 16053 | 1.09 | 61 |
| P3HT-Br L | 25976 | 28866 | 1.11 | 106 |

The molecular weight and dispersity of P3 HT-Br were varied due to the quality of monomer, catalytic reagents and lab conditions. Three sizes of P3 HT-Br were obtained by varying the loading of catalyst amounts.

General Synthesis of Functionalized Polythiophenes

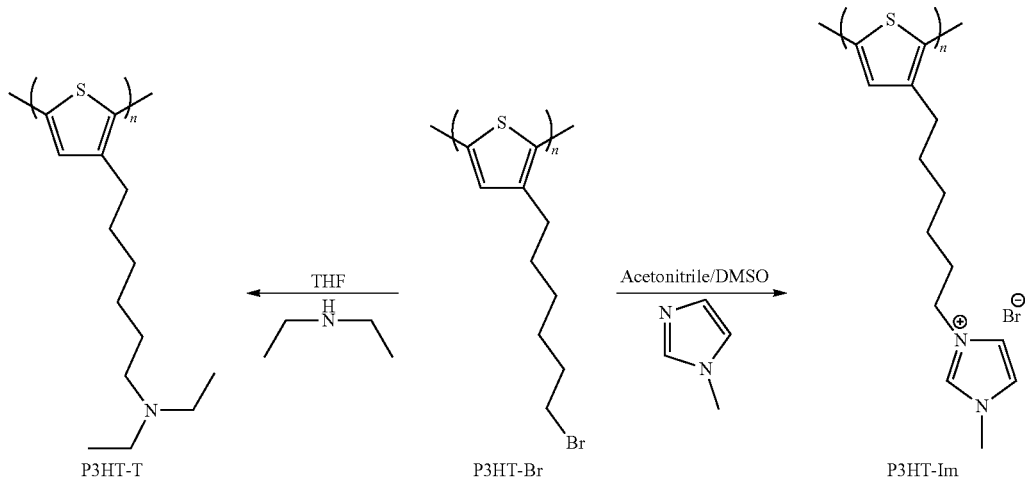

Scheme 2. Synthesis route of P3HT-Im and P3HT-T.

The synthesis of P3 HT-Im and P3 HT-T is depicted in Scheme 2. Both types of functionalized polythiophene were prepared from an alkylbromide-substituted polythiophene.

The resulting polymers were not easily examined by GPC, due to the strong ionic interactions between polymer and GPC column. The molecular weight of P3 HT-T and P3 HT-Im was calculated using the molecular weight information of P3 HT-Br, as the degrees of polymerization and polydispersity of the polymers do not change after functionalization. All bromine atoms were ionized with imidazolium or substituted by diethylamine groups, which was verified by 1H NMR. Compared with 1H NMR spectra of P3 HT-Br, well-integrated peaks in aromatic region in 1H NMR spectra of P3 HT-Im, indicating the full ionization of bromine by imidazolium. Compared with 1H NMR spectra of P3 HT-Br, the complete disappearance of a triplet peak at 3.43 ppm in 1H NMR spectra of P3 HT-T, indicating the full substitution of bromine by diethylamine groups. The calculated molecular weight of P3 HT-Im and P3 HT-T is summarized in Tables 2 and 3.

Mn refers to number-average molecular weight estimated from gel permeation chromatography (GPC); Mw refers to weight-average molecular weight estimated from GPC; PDI refers to polydispersity index; DP is average degree of polymerization estimated from Mn values, where molecular weight per repeat unit of the P3 HT-Br is 245.2 g/mol. The Mn of P3 HT-Im and P3 HT-T was calculated from corresponding P3 HT-Br, assuming DP and PDI did not change after functionalization. The molecular weights per repeat unit (pru) of the P3 HT-Im and P3 HT-T are 327.3 g/mol and 237.4 g/mol, respectively. Since antimicrobial activity was tabulated in terms of micrograms per milliliter (µg/mL), for each sample there are somewhat more pru's for each sample of P3 HT-T as compared with P3 HT-Im.

Synthesis of P3 HT-Im

P3 HT-Im was synthesized by reaction P3 HT-Br with excess n-methylimidazole. Three different sizes of P3 HT-Im were generated from the corresponding small, medium and large P3 HT-Br as shown in Table 2.

TABLE 2

Calculated Molecular Weight of P3HT-Im (including Br⁻ counterion)

| Polymer | Mn (Da) | PDI | DP |
| --- | --- | --- | --- |
| Shortest | | | 5 |
| P3HT-Im S | 3600 | 1.21 | 11 |
| P3HT-Im M | 19965 | 1.09 | 61 |
| P3HT-Im L | 34694 | 1.11 | 106 |

P3 HT-Im was synthesized by reaction P3 HT-Br with excess n-methylimidazole. Three different sizes of P3 HT-Im were generated from the corresponding P3 HT-Br.

Synthesis of P3 HT-T

P3 HT-T was synthesized by reacting P3 HT-Br with excess diethylamine. Three different sizes of P3 HT-T were generated from the corresponding P3 HT-Br, as shown in Table 3.

TABLE 3

Calculated Molecular Weight of P3HT-T

| Polymer | Mn (Da) | PDI | DP |
| --- | --- | --- | --- |
| P3HT-T S | 2611 | 1.21 | 11 |
| P3HT-T M | 14481 | 1.09 | 61 |
| P3HT-T L | 25164 | 1.11 | 106 |

Effects of Polythiophene Size on Light Absorbance and Emission.

It was observed that the polythiophenes of the present disclosure provided different properties as size increased. The absorbance and emission properties of P3 HT-Im were measured to quantify this phenomenon. This is shown in FIG. 1.

As polymer size increased up to about 106 repeat units, absorbance spread further across the visible light range. At the lowest range of polymer sizes, absorbance as predominantly in the in the ultraviolet range with only a minor proportion of absorbance light in the visible range. The shortest polymer chain (5 repeat units) showed absorbance peaking around 400 nm and showed emission peaking around 550 nm. These polythiophenes displayed as green under UV light. The example of a short polythiophene (11 repeat units) showed absorbance peaking around 425 nm and showed emission peaking around 575 nm. These polythiophenes displayed as yellow under UV light. The example of a medium polythiophene (60 repeat units) showed absorbance peaking around 450 nm and showed emission peaking around 600 nm. These polythiophenes displayed as orange under UV light. The example of a medium polythiophene (106 repeat units) showed absorbance peaking around 475 nm and showed emission peaking around 600 nm. These polythiophenes displayed as red under UV light. These results demonstrate that once the polythiophenes reach medium size or larger, the absorbance range of the compound has a maximum absorbance in the range of 450-475 and a majority of the absorbance spectrum is within the visible range. Maximizing absorbance in the visible range is advantageous for use of the polythiophenes as passive disinfectants.

The size-dependent effect on light absorbance and emission of polythiophenes was also demonstrated by visual inspection. P3 HT-Im with 20 µg/mL solutions in natural light appear yellow (small), orange (medium) or clear (large) and in UV appear yellow (small) or red (medium and large). P3 HT-T with 20 µg/mL solutions in natural light appear yellow (small) or orange (medium and large) and in UV appear orange (small) or red (medium and large). This result demonstrates the redshift of absorbance and emission as polymer size increases. The indicated sizes correspond to the degree of polymerization where small is ≈11 DP, medium is ≈61 DP and large is ≈106 DP.

Effects of Polythiophene Size on Antibacterial Activity.

Figure 3:
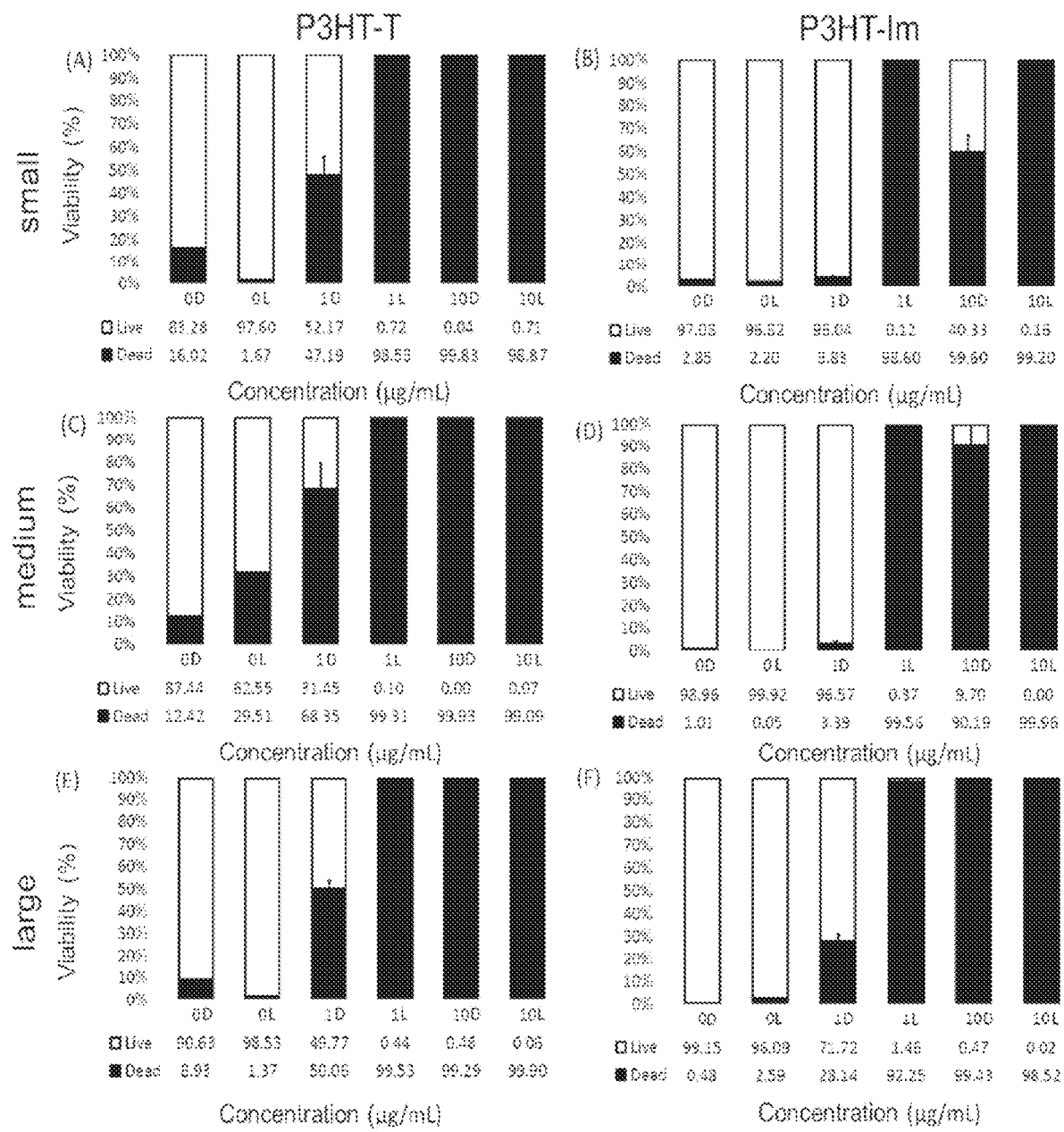
FIG. 3 shows the results of flow cytometry viability assays of P3 HT-T and P3 HT-Im on *B. atrophaeus* as follows: (A) cell viability after exposure to small P3 HT-T in dark and light conditions; (B) cell viability after exposure to small P3 HT-Im in dark and light conditions; (C) cell viability after exposure to medium P3 HT-T in dark and light conditions; (D) cell viability after exposure of medium P3 HT-Im in dark and light conditions; (E) cell viability after exposure to large P3 HT-T in dark and light conditions; (F) cell viability after exposure to large P3 HT-Im in dark and light conditions, where cell viability is given as the y-axis, concentration of polymer is given as the x-axis, and L or D indicates light exposure or dark conditions respectively.
Figure 4:
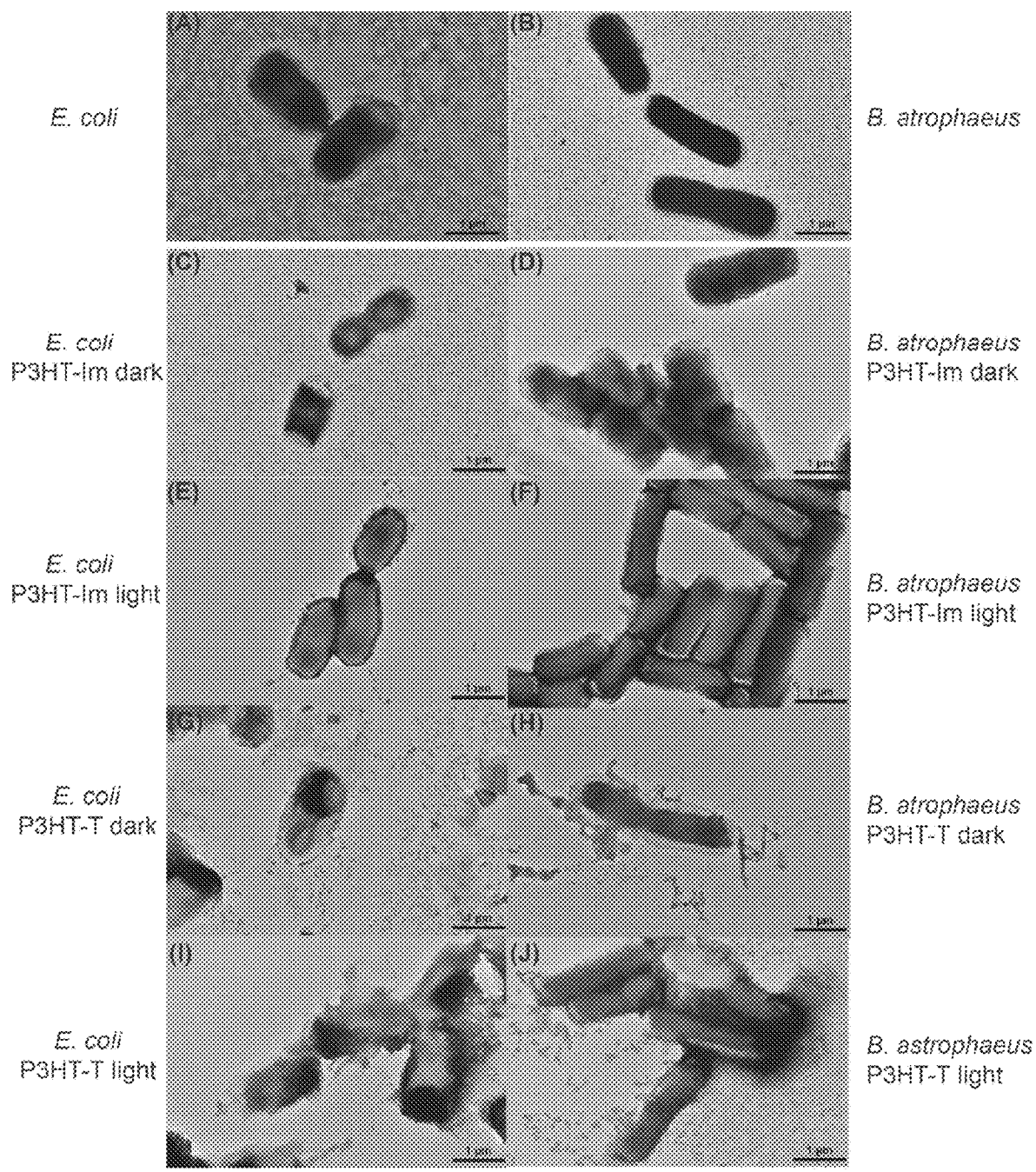
FIG. 4 shows TEM images of *E. coli* and *B. atrophaeus* as follows: (A) *E. coli* without exposure to polymer; (B) *B. atrophaeus* without exposure to polymer; (C) *E. coli* exposed to P3 HT-Im under dark conditions; (D) *B. atrophaeus* exposed to P3 HT-Im in dark conditions; (E) *E. coli* exposed to P3 HT-Im after irradiation with blue-violet light; (F) *B. atrophaeus* exposed to P3 HT-Im after irradiation with blue-violet light; (G) *E. coli* exposed to P3 HT-T under dark conditions; (H) *B. atrophaeus* exposed to P3 HT-T in dark conditions; (I) *E. coli* exposed to P3 HT-T after irradiation with blue-violet light; (J) *B. atrophaeus* exposed to P3 HT-T after irradiation with blue-violet light.

The antibacterial properties of different sizes of P3 HT-Im and P3 HT-T were measured using flow cytometry under either light exposure or dark conditions, at various concentrations of polymer. Results are shown in FIG. 2, FIG. 3 and FIG. 4.

The flow cytometry viability assays were used to assess the percent killing of E. coli and B. atrophaeus after exposure to polymers under photolysis and dark conditions using live/dead stains. The following results assess the capability of each polymer size to kill the bacterial species at concentrations of 1 and 10 µg/mL in irradiated and dark conditions.

Figure 2:
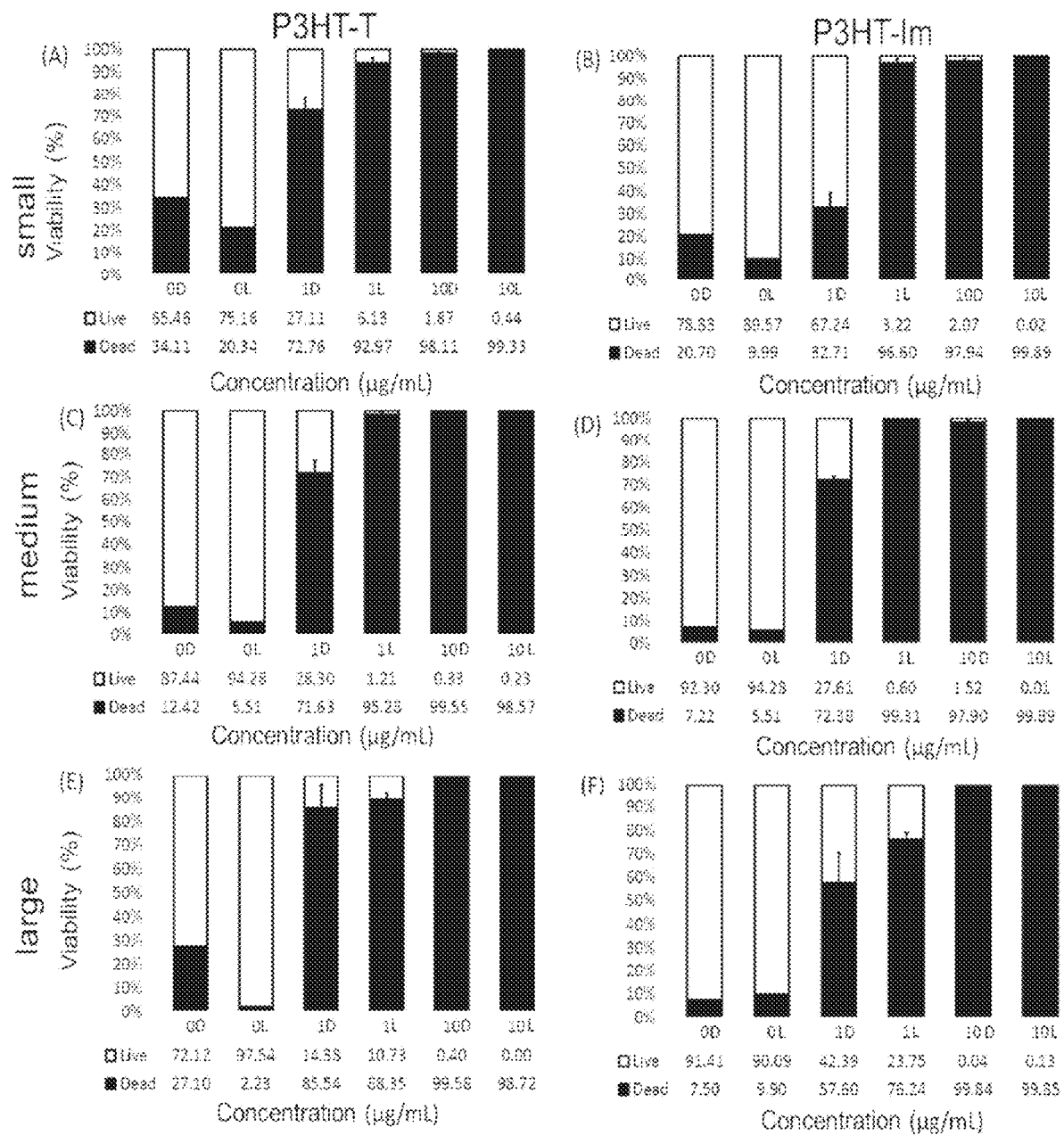
FIG. 2 shows the results of flow cytometry viability assays of P3 HT-T and P3 HT-Im on *E. coli* as follows: (A) cell viability after exposure to small P3 HT-T in dark and light conditions; (B) cell viability after exposure to small P3 HT-Im in dark and light conditions; (C) cell viability after exposure to medium P3 HT-T in dark and light conditions; (D) cell viability after exposure of medium P3 HT-Im in dark and light conditions; (E) cell viability after exposure to large P3 HT-T in dark and light conditions; (F) cell viability after exposure to large P3 HT-Im in dark and light conditions, where cell viability is given as the y-axis, concentration of polymer is given as the x-axis, and L or D indicates light exposure or dark conditions respectively.

Against E. coli, both small and medium P3 HT-Im and P3 HT-T show high rates of killing at concentrations of 1 µg/mL and 10 µg/mL under photolysis, shown in FIG. 2. Under dark conditions P3 HT-T shows similar percentages of killing at 1 µg/mL when compared with P3 HT-Im with the highest percentage achieved for medium derivatives at 95.28%±0.53 (P3 HT-T) and 99.31%±0.10 (P3 HT-Im). At 10 µg/mL there is no significant difference between P3 HT-T and P3 HT-Im under dark conditions for each polymer size. P3 HT-Im at 10 µg/mL shows slightly higher percentages of killing under photolysis when compared with P3 HT-T. Greater than 97% killing is observed for all samples under photolysis and in dark conditions at this concentration. This is shown in FIG. 2.

FIG. 2 shows the results of flow cytometry viability assays of P3 HT-T and P3 HT-Im on E. coli where viability is given as the y-axis, concentration of polymer is given as the x-axis, and L or D indicates light exposure or dark conditions respectively. Samples were either irradiated or kept in dark conditions for 1 h then stained for 30 minutes. The results are arranged as follows: (A) Cell viability after exposure to small P3 HT-T in dark and light conditions; (B) Cell viability after exposure to small P3 HT-Im in dark and light conditions; (C) Cell viability after exposure to medium P3 HT-T in dark and light conditions; (D) Cell viability after exposure of medium P3 HT-Im in dark and light conditions; (E) Cell viability after exposure to large P3 HT-T in dark and light conditions; and (F) Cell viability after exposure to large P3 HT-Im in dark and light conditions. Error is reported as the standard deviation of 3 samples.

These results show a greater effect on antimicrobial activity by photoactivation on the polymers at lower polymer concentrations. Without being limited by theory, it is thought that for each polymer at concentrations of 1 µg/mL the generation of singlet oxygen contributes to significant increased biocidal activity against E. coli. The ability for the polymers to generate singlet oxygen was shown by use of 9, 10-anthracenediyl-bis(methylene) dimalonic acid (ADMA) as a sensor to detect the presence of singlet oxygen via a cycloaddition reaction.

Substantial bactericidal activity was seen for both tested polymers. Without being limited by theory, it is thought that for gram-negative E. coli, lipopolysaccharides containing negatively charged carboxyl groups and inorganic phosphates may provide points of interaction for P3 HT-T and P3 HT-Im leading to membrane damage. This is independent of polymer functionalization and light condition.

Against B. atrophaeus, both polymer types showed high rates of killing at 1 µg/mL under photolysis. Reduced killing was observed for dark samples at 1 µg/mL for both P3 HT-T and P3 HT-Im in comparison to photolysis conditions. The large differences in dark killing between P3 HT-T and P3 HT-Im for this species of bacteria at concentrations of 1 µg/mL was seen at a lesser extent for E. coli, however, the trend of higher killing by P3 HT-T in dark conditions still held. Dark killing was higher for P3 HT-T at 10 µg/mL compared to P3 HT-Im in the dark for this strain of bacteria. This is shown in FIG. 3.

FIG. 3 shows the results of flow cytometry viability assays of P3 HT-T and P3 HT-Im on B. atrophaeus where viability is given as the y-axis, concentration of polymer is given as the x-axis, and L or D indicates light exposure or dark conditions respectively. Samples were either irradiated or kept in dark conditions for 1 h then stained for 30 minutes. The results are arranged as follows: (A) Cell viability after exposure to small P3 HT-T in dark and light conditions; (B) Cell viability after exposure to small P3 HT-Im in dark and light conditions; (C) Cell viability after exposure to medium P3 HT-T in dark and light conditions; (D) Cell viability after exposure of medium P3 HT-Im in dark and light conditions; (E) Cell viability after exposure to large P3 HT-T in dark and light conditions; and (F) Cell viability after exposure to large P3 HT-Im in dark and light conditions. Error is reported as the standard deviation of 3 samples.

Greater than 98% killing was achieved for P3 HT-T at 10 µg/mL under dark and photolytic conditions and P3 HT-Im under photolytic conditions. Unlike results pertaining to E. coli, as low as 59.60%±7.02 killing was observed for P3 HT-Im at 10 µg/mL in the case of the small derivative. Still, substantial antimicrobial activity was observed under photolysis for concentrations of 1 and 10 µg/mL and in many cases for 10 µg/mL in dark conditions. This shows the capability of these polymers to act as antimicrobial materials for both Gram-positive and Gram-negative bacteria at similar capacity.

It is noted that the amount of killing observed from large P3 HT-T poses higher uncertainty due to possibility of crystalline aggregates forming in solution depending on solution conditions. Though relatively high rates of killing are observed with this polymer, it is a possibility that the aggregation state of the polymer may play a role in the killing of bacteria across samples. This polymer is not easily solubilized, though tested samples were solubilized as much as possible without introducing solvents other than water in to the system.

Visualization of Antibacterial Effects

TEM images were acquired to investigate possible differences in membrane damage caused by P3 HT-T and P3 HT-Im under photolytic and dark conditions. For both microbial species, TEM images were taken after exposure 10 to 10 µg/mL of medium sized polymer exposed to blue-violet light for 1 h or dark conditions for 1 h. Control images were not exposed to polymer. Additionally, B. atrophaeus is a spore forming species and TEM is used to ensure the presence of polymer does not cause sporulation in the sample populations, which could lead to vegetation upon the re-introduction of nutrients to the system. This is shown in FIG. 4.

FIG. 4 shows the results of TEM images of E. coli and B. atrophaeus with exposure to 10 µg/mL of medium P3 HT-T and P3 HT-Im under photolysis and dark conditions. The images are arranged as follows: (A) E. coli without exposure to polymer; (B) B. atrophaeus without exposure to polymer; (C) E. coli exposed to P3 HT-Im under dark conditions; (D) B. atrophaeus exposed to P3 HT-Im in dark conditions; (E) E. coli exposed to P3 HT-Im after irradiation with blue-violet light; (F) B. atrophaeus exposed to P3 HT-Im after irradiation with blue-violet light; (G) E. coli exposed to P3 HT-T under dark conditions; (H) B. atrophaeus exposed to P3 HT-T in dark conditions; (I) E. coli exposed to P3 HT-T after irradiation with blue-violet light; and (J) B. atrophaeus exposed to P3 HT-T after irradiation with blue-violet light.

Membrane damage caused by P3 HT-T samples is visibly greater under irradiation compared to P3 HT-Im for both microbial species (FIG. 4: E, F, I, J). While membrane damage can be seen from P3 HT-Im, P3 HT-T light exposure causes intracellular contents to evacuate the cells more aggressively, shown by portions of the cell images that appear lighter in color and the amount of cell debris. P3 HT-T also shows higher membrane damage under dark conditions (FIG. 4: C, D, G, H) compared to P3 HT-Im, which appears minimally damaging in the dark. Both polymers show higher membrane damage to the cells under irradiation when compared with the control and dark conditions. All four panels with P3 HT-T show external debris organized in a way that may show association of protonated P3 HT with cellular components. This is not seen for P3 HT-Im images.

Polythiophenes of Various Sizes with Anionic Scaffolds

The polythiophenes of the present disclosure form complexes with anionic scaffolds, such as carboxymethyl amylose (CMA) and carboxymethyl cellulose (CMC), and with anionic detergents, such as sodium dodecylsulfate (SDS).

P3 HT-Im of various sizes were complexed with amylose and with cellulose.

For the shortest P3 HT-Im, increasing amounts of CMA showed an effect of shifting emission toward lower wavelengths and reducing intensity. Increasing amounts of CMC showed an effect of drastically reducing intensity.

For the small (11 repeat unit) P3 HT-Im, increasing amounts of CMA showed an effect of shifting emission further toward lower wavelengths and showed some increase and some decrease in intensity. Increasing amounts of CMC showed an effect of shifting emission toward higher wavelengths and a reduction in intensity.

For the medium (60 repeat unit) P3 HT-Im, increasing amounts of CMA showed an effect of substantially shifting emission toward lower wavelengths while strongly increasing intensity. Increasing amounts of CMC showed an effect of slightly shifting emission toward higher wavelengths with and a reduction in intensity.

For the large (106 repeat unit) P3 HT-Im, increasing amounts of CMA showed an effect of substantially shifting emission toward lower wavelengths and showed some increase and some decrease in intensity. Increasing amounts of CMC showed an effect of slightly shifting emission toward higher wavelengths with and a reduction in intensity.

P3 HT-Im (5 repeat units) and (106 repeat units) were also complexed with sodium dodecylsulfate (SDS). The larger P3 HT-Im shows significant changes in color, which is thought, without being limited to theory, to reflect that when under critical micelle concentration red shift occurs, upon reaching charge neutrality coacervate forms, and above critical micelle concentration blue shift occurs and micelles form.

Stable Hydrogel Compositions with Polythiophenes

Figure 5:
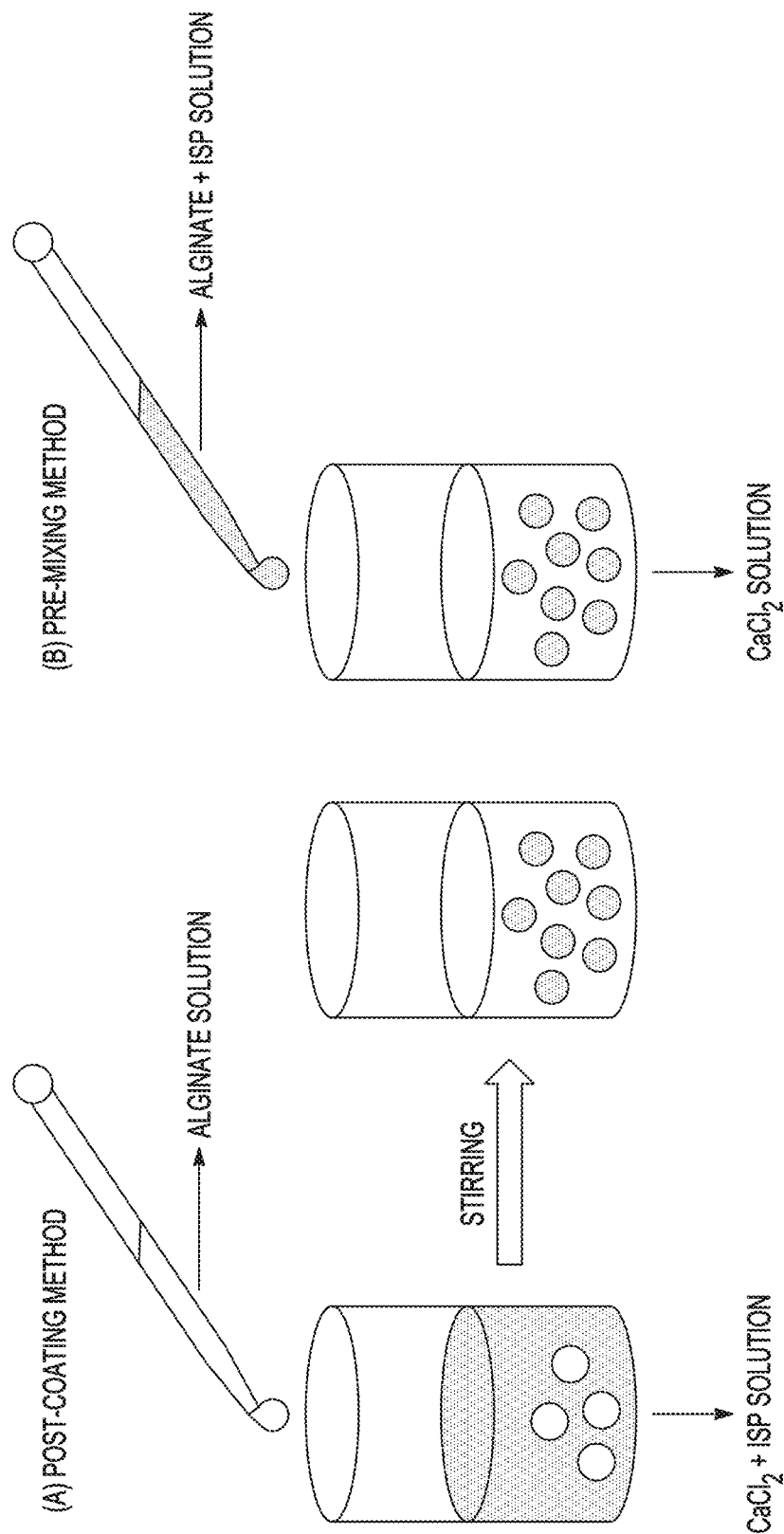
FIG. 5 is an illustration showing two methods of preparing polythiophene hydrogels: (A) a post-coating method and (B) a pre-mixing method.

Stable hydrogel compositions were prepared from a polythiophene (P3 HT-Im), alginate and calcium chloride. The hydrogels were prepared by two methods, a post-coating method or a pre-mixing method. In the post-coating method, an alginate solution is added to a solution of calcium chloride and polythiophene in water. The resulting mixture is stirred and results in a calcium chloride solution having polythiophene-containing hydrogel globules. In the pre-mixing method, a pre-mixed solution of alginate and polythiophene is added to a solution of calcium chloride in water to directly result in the polythiophene hydrogel globules. An illustration of the two methods and a photograph of the polythiophene-containing hydrogel are shown in FIG. 5.

Discussion

The examples above demonstrate that the polythiophenes described herein are potent antibacterial agents. Comparing the antimicrobial activity against the two bacteria, irradiated samples of P3 HT-T and P3 HT-Im killed nearly 100% of E. coli and B. atrophaeus at concentrations of 10 µg/mL. High killing was also observed in the irradiated samples with concentrations of 1 µg/mL for both species and polymer types, greater than 90% in all cases except for E. coli with long polymer constituents.

Without being limited to theory, it is thought that cationic polythiophenes have the ability to selectively associated with and damage negatively charged cell envelopes, such as the cell envelopes of bacteria. Antibacterial activity was demonstrated for polythiophenes having permanent cations such as imidazolium and also cations resulting from protonation such as trialkylammonium. It is further thought that the antibacterial properties of these polythiophenes may arise from their ability to absorb light and sensitize the production of reactive oxygen species (ROS). This study further demonstrates the ability of differentially sized imidazolium and tertiary amine functionalized poly(3-hexylthiophene) (P3 HT) to inactivate Gram-negative Escherichia coli and Gram-positive Bacillus atrophaeus under photolysis and dark conditions. Prior to these results, it was not known what effect polymer chain length would have on antibacterial activity, particularly what would be the effect of polythiophenes having a particular chain length and a low polydispersity index. Additionally, the results herein show successful results for even the largest and smallest tested polythiophenes at 1 µg/cm$^3$ to 10 µg/cm$^3$ (e.g., 1 µg to 10 µg per ml or g of a water-based composition).

Studies on phenylene-ethynynlene polymers (PPE) and oligomers (OPE) had previously shown that increased polymer size and concentration reduced bactericidal activity, which was attributed to aggregation of the larger polymers. (Ji et al., 2011). Surprisingly, increased polymer size and concentration of imidazolium and dialkylamine based polythiophenes did not show any problems of reduced bactericidal activity. In fact, in some of the examples herein bactericidal activity was improved when using larger polythiophenes. Polythiophenes of larger sizes offer certain advantages for various applications. For example, larger polythiophenes will be broken down more slowly, remain embedded in materials for longer, will not readily wash away when exposed to water, solvent or detergent, and may offer improved visible light absorption. As another example, smaller polythiophenes such as oligomers were shown to largely maintain bactericidal activity. Such smaller polythiophenes have the advantage of more readily being removed from a given substrate whether by being easily deposited or by being washed off, than those providing temporary antibacterial coatings or providing substrates which deposit antibacterial agents on a surface such as a disinfecting wipe or spray. Such smaller polythiophenes also may have more limited visible light absorption, which can provide an antibacterial substrate or method which can activate the antibacterial activity only on demand. Such smaller polythiophenes may also be more readily decomposed than larger polythiophenes. However, prior to the examples herein, it was not recognized that certain size ranges of polythiophene would have maintained or improved bactericidal activity. In various embodiments of the present invention, limiting the included polythiophenes to certain sizes results in improved antibacterial substrates, improved methods of disinfecting and improved disinfectants. Notably, many advantages can arise from use of polythiophenes having a size distribution including polythiophenes having 13 or fewer repeating units, polythiophenes having 30 or greater repeating units, or both.

Additionally, tertiary amine-functionalized polythiophene was shown to have different killing patterns as compared to the imidazolium functionalized derivatives. TEM images discussed above showed that P3 HT-T damages bacterial cell membranes of both bacteria more aggressively than P3 HT-Im. Such results show the strong potential for neutral polymers and oligomers to act as biocides. The results of this study clearly support that the protonation state of several of the tertiary amine groups in the P3 HT-T polymers in aqueous media renders them biocidal towards both Gram-negative and Gram-positive bacteria. Interestingly, TEM images of P3 HT-T show visible differences in cell and membrane debris organization. The major differences in membrane damage between tertiary amine and imidazolium functionalized polymers is considered to arise due to the ability of tertiary amines to reversibly protonate. The tertiary amine functionalization provides increased membrane damage on bacteria independent of light activation and acts as a potent antimicrobial without light activation. These findings suggest that this class of polymers can be used in a variety of applications with potential to diversify the uses of P3 HT-T and P3 HT-Im polymers. For example, imidazolium-based polythiophenes may be more advantageously used if contact with mammalian cells is likely, because the cation is always present, and the resulting selectivity will be specific to bacterial membranes.

Various polythiophene polymers also show substantial bactericidal activity in the dark, with potentially different products from the photolysis products, thus showing that the polythiophenes described herein can be used in dark environments and applications without requiring any photolysis or irradiation step.

Various polythiophene polymers described herein absorb strongly in the visible range and may react by passively absorbing room light or sunlight which would be advantageous for surface coatings which are passively bactericidal. As discussed above, larger polythiophenes can advantageously improve the amount of absorption in the visible range without loss of antibacterial activity.

The potential ability for amine-functionalized polythiophenes to organize cellular debris may be advantageous in applications towards use as biosensors or drug delivery agents in conjunction with polymer-micelle or liposome structures.

Overall, the examples provided herein demonstrate that polythiophenes having either cationic or neutral functional groups and having certain ranges of polymer sizes provide unexpected advantages for certain applications.

Preparation of Disinfecting Wipes

Kimwipes® (Kimberly-Clark) or similar textiles are used as the primary substrate. Kimwipes® measuring 9 in² are granted antimicrobial properties upon being exposed to a high concentration of polythiophene. The polythiophene is dissolved in a combination of deionized water and dimethyl sulfoxide such that the final concentration is approximately 4 mg/mL. About 200 μL of the polythiophene solution is then distributed across the surface area of a 9 in² Kimwipe® textile such that the entire textile appears saturated. The treated Kimwipe® textile is then permitted up to about 18 hours to fully dry.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present invention.

ADDITIONAL EMBODIMENTS

The following exemplary embodiments are provided, the numbering of which is not to be construed as designating levels of importance:

Embodiment 1 provides an antimicrobial substrate, comprising a substrate and a polythiophene having the structure

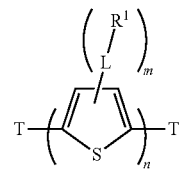

wherein
R¹ is

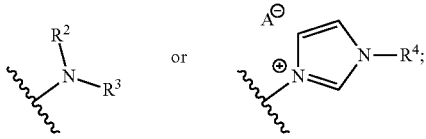

each of $R^2$ and $R^3$ is independently $C_1$-$C_6$ alkyl or $R^2$ and $R^3$ taken together are linked $C_2$-$C_5$ alkyl which forms a 3 to 6-membered saturated heterocyclic ring together with the nitrogen at which they attach;

$R^4$ is $C_1$-$C_6$ alkyl;

A is a counterion;

L is a divalent $C_1$-$C_{20}$ alkyl linker, optionally interrupted by 1, 2 or 3 oxygen, sulfur or nitrogen atoms;

T is a terminal group;

m is 1-2;

n is 30 to 120;

the polythiophene has a number average molecular weight (Mn) from 10,000 to 40,000; and the polythiophene has a polydispersity index (PDI) is from 1 to 1.3.

Embodiment 2 provides the antimicrobial substrate of Embodiment 1, wherein the number average molecular weight (Mn) is 20,000 to 40,000, n is 50 to 110, and the polydispersity index (PDI) is from 1 to 1.25

Embodiment 3 provides the antimicrobial substrate of Embodiment 1 or 2, wherein is at least 60.

Embodiment 4 provides the antimicrobial substrate of any one of Embodiments 1-3, wherein about 1 μg/cm³ to about 10 μg/cm³ of the antimicrobial substrate is the polythiophene.

Embodiment 5 provides the antimicrobial substrate of any one of Embodiments 1-4, wherein $R^1$ is

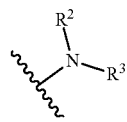

and $R^2$ and $R^3$ is each ethyl.

Embodiment 6 provides the antimicrobial substrate of any one of Embodiments 1-5, wherein $R^1$ is

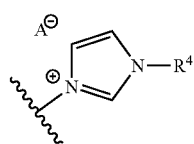

and $R^4$ is methyl.

Embodiment 7 provides the antimicrobial substrate of any one of Embodiments 1-6, wherein L is hexyl.

Embodiment 8 provides the antimicrobial substrate of any one of Embodiments 1-7, wherein the substrate is a wipe, a tissue, a bandage, a medical device, surgical instrument, tubing, a catheter, warfighter machinery, a sponge, a textile, a diaper, a counter-top, a food preparation surface, a wound dressing, a dressing for surgical incisions, a keyboard surface, a packing for wounds, a packing for surgical incisions, a nasal packing or a feminine care product, or a combination thereof.

Embodiment 9 provides the antimicrobial substrate of any one of Embodiments 1-8, wherein the substrate is a wipe.

Embodiment 10 provides the antimicrobial substrate of any one of Embodiments 1-9, wherein the polythiophene provides a temporary antimicrobial coating on the substrate which is removable by treatment with one or more of water, organic solvent, base and detergent.

Embodiment 11 provides the antimicrobial substrate of any one of Embodiments 1-10, wherein the polythiophene is embedded in the substrate and remains at a concentration of about from about 0.1 μg/cm³ to about 10 μg/cm³ after washing the antimicrobial substrate.

Embodiment 12 provides the antimicrobial substrate of any one of Embodiments 1-11, wherein the polythiophene absorbs visible light.

Embodiment 13 provides the antimicrobial substrate of any one of Embodiments 1-12, wherein the substrate is a polysaccharide.

Embodiment 14 provides the antimicrobial substrate of any one of Embodiments 1-13, wherein the polysaccharide is alginate, carboxymethyl amylose or carboxymethyl cellulose.

Embodiment 15 provides the antimicrobial substrate of any one of Embodiments 1-14, wherein it is in the form of a hydrogel.

Embodiment 16 provides the antimicrobial substrate of any one of Embodiments 1-15, further comprising at least one of a detergent, a calcium salt and a copper salt.

Embodiment 17 provides a polythiophene polymer having the structure:

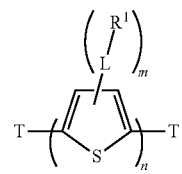

wherein $R^1$ is

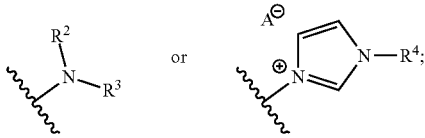

each of $R^2$ and $R^3$ is independently $C_1$-$C_6$ alkyl or $R^2$ and $R^3$ taken together are linked $C_2$-$C_5$ alkyl which forms a 3 to 6-membered saturated heterocyclic ring together with the nitrogen at which they attach;

$R^4$ is $C_1$-$C_6$ alkyl;

A is a counterion;

L is a divalent $C_1$-$C_{20}$ alkyl linker, optionally interrupted by 1, 2 or 3 oxygen, sulfur or nitrogen atoms;

T is a terminal group;

m is 1-2;

n is 5-14 or 30 to 120;

the polythiophene polymer has a number average molecular weight (Mn) from 1,000 to 4,000 or 10,000 to 40,000; and the polythiophene polymer has a polydispersity index (PDI) from 1 to 1.3

Embodiment 18 provides a method of disinfecting, comprising treating a surface with a disinfectant composition which comprises a carrier and a polythiophene having the structure

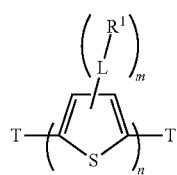

wherein
R¹ is

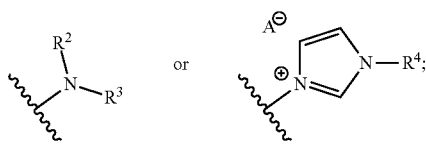

each of R² and R³ is independently C₁-C₆ alkyl or R² and R³ taken together are linked C₂-C₅ alkyl which forms a 3 to 6-membered saturated heterocyclic ring together with the nitrogen at which they attach;

R⁴ is C₁-C₆ alkyl;

A is a counterion;

L is a divalent C₁-C₂₀ alkyl linker, optionally interrupted by 1, 2 or 3 oxygen, sulfur or nitrogen atoms;

T is a terminal group;

m is 1-2;

n is 5-14 or 30 to 120;

the polythiophene has a number average molecular weight (Mn) is from 1,000 to 4,000 or 10,000 to 40,000; and the polythiophene has a polydispersity index (PDI) is from 1 to 1.3.

Embodiment 19 provides the method of Embodiment 18, wherein the area is treated with the disinfectant composition via a spray, a lotion, a dip, a bath, or by contact with a substrate saturated with the disinfectant composition.

Embodiment 20 provides the method of Embodiment 18 or 19, wherein the carrier is water having a pH of 6-8.

Embodiment 21 provides the polythiophenes, method, or antimicrobial substrate of any one or any combination of Embodiments 1-20 optionally configured such that all elements or options recited are available to use or select from.

What is claimed is:

1. A polythiophene having the structure:

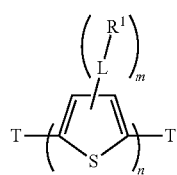

wherein
R¹ is

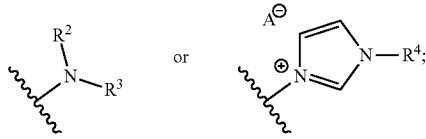

each of R² and R³ is independently C₁-C₃ alkyl;

R⁴ is C₁-C₃ alkyl;

A is a counterion;

L is a divalent C₁-C₆ alkyl linker;

T is a terminal group;

m is 1;

n is 5 to 14, or 30 to 120;

the polythiophene has a number average molecular weight (Mn) from 1,000 to 4,000, or from 10,000 to 40,000; and the polythiophene has a polydispersity index (PDI) of from 1 to 1.25.

2. The polythiophene of claim 1, wherein the polythiophene has a PDI of 1.08 to 1.22.

3. The polythiophene of claim 1, wherein n is 50 to 110.

4. The polythiophene of claim 1, wherein n is at least 60.

5. The polythiophene of claim 1, wherein n is 5 to 14.

6. The polythiophene of claim 1, wherein n is 30 to 120.

7. The polythiophene of claim 1, wherein the polythiophene has a number average molecular weight (Mn) from 1,000 to 4,000.

8. The polythiophene of claim 1, wherein the polythiophene has a number average molecular weight (Mn) from 10,000 to 40,000.

9. The polythiophene of claim 1, wherein L is —(CH₂)₆—.

10. The polythiophene of claim 1, wherein R¹ is

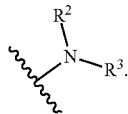

11. The polythiophene of claim 1, wherein R² and R³ are each ethyl.

12. The polythiophene of claim 1, wherein R¹ is

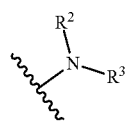

and R² and R³ are each ethyl.

13. The polythiophene of claim 1, wherein R¹ is

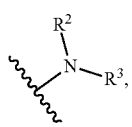

R² and R³ are each ethyl, and L is —(CH₂)₆—.

14. The polythiophene of claim 1, wherein R¹ is

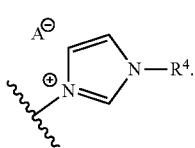

15. The polythiophene of claim 1, wherein R⁴ is methyl.

16. The polythiophene of claim 1, wherein $R^1$ is

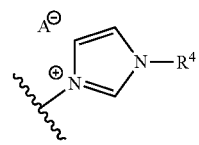

and $R^4$ is methyl.

17. The polythiophene of claim 1, wherein $R^1$ is

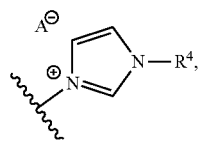

$R^4$ is methyl, and L is —$(CH_2)_6$—.

18. The polythiophene of claim 1, wherein T is independently chosen from —H and $(C_1\text{-}C_{10})$hydrocarbyl.

19. The polythiophene of claim 1, wherein $A^-$ is chloride, bromide, iodide, sulfate, phosphate, sulfite, phosphite, or carbonate.

20. The polythiophene of claim 1, wherein $A^-$ is $Br^-$.

* * * * *